United States Patent
Kettle et al.

(10) Patent No.: US 6,569,888 B1
(45) Date of Patent: May 27, 2003

(54) ANTI-INFLAMMATORY INDOLE DERIVATIVES

(75) Inventors: Jason Kettle, Macclesfield (GB); Alan W Faull, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/889,494

(22) PCT Filed: Jan. 31, 2000

(86) PCT No.: PCT/GB00/00275

§ 371 (c)(1),
(2), (4) Date: Sep. 12, 2001

(87) PCT Pub. No.: WO00/46198

PCT Pub. Date: Aug. 10, 2000

(30) Foreign Application Priority Data

Feb. 5, 1999 (GB) ............................................. 9902452

(51) Int. Cl.⁷ ..................... C07D 209/22; A61K 31/404
(52) U.S. Cl. ..................... 514/419; 514/380; 514/381; 514/228.2; 548/492; 548/243; 548/252; 548/253; 548/493; 548/466; 544/58.1
(58) Field of Search .................... 548/466, 243, 548/493, 252, 492, 253; 514/228.2, 419, 414, 380, 381

(56) References Cited

U.S. PATENT DOCUMENTS

| | | |
|---|---|---|
| 3,557,142 A | 1/1971 | Bell |
| 3,776,923 A | 12/1973 | Remers et al. |
| 3,997,557 A | 12/1976 | Helsley et al. |
| 4,529,724 A | 7/1985 | Ho |
| 4,608,384 A | 8/1986 | Wierzbicki et al. |
| 4,721,725 A | 1/1988 | Biller et al. |
| 4,751,231 A | 6/1988 | Halczenko et al. |
| 4,965,369 A | 10/1990 | Maetzel et al. |
| 5,081,145 A | 1/1992 | Guindon et al. |
| 5,190,968 A | 3/1993 | Gillard et al. |
| 5,254,563 A | 10/1993 | Huth et al. |
| 5,272,145 A | 12/1993 | Prasit et al. |
| 5,273,980 A | 12/1993 | Frenette et al. |
| 5,288,743 A | 2/1994 | Brooks et al. |
| 5,290,798 A | 3/1994 | Gillard et al. |
| 5,308,850 A | 5/1994 | Gillard et al. |
| 5,389,650 A | 2/1995 | Frenette et al. |
| 5,399,699 A | 3/1995 | Kolasa et al. |
| 5,482,960 A | 1/1996 | Berryman et al. |
| 5,684,032 A | 11/1997 | Elliott et al. |
| 5,852,046 A | 12/1998 | Lang et al. |
| 5,955,492 A | 9/1999 | Thompson et al. |
| 6,184,235 B1 | 2/2001 | Connor et al. |
| 6,337,344 B1 * | 1/2002 | Defossa et al. ............. 514/415 |

FOREIGN PATENT DOCUMENTS

| | | |
|---|---|---|
| DE | 298 913 a5 | 3/1992 |
| EP | 0 077 209 | 4/1983 |
| EP | 0 186 367 | 7/1986 |
| EP | 0 189 690 | 8/1986 |
| EP | 0 419 049 A1 | 3/1991 |
| EP | 0 480 659 A2 | 4/1992 |
| EP | 0 535 923 A1 | 4/1993 |
| EP | 0 535 924 A1 | 4/1993 |
| EP | 0 535 925 A1 | 4/1993 |
| EP | 0 535 926 A1 | 4/1993 |
| EP | 0 639 537 | 2/1995 |
| EP | 0 639 573 A1 | 2/1995 |
| EP | 0 822 185 | 2/1998 |
| EP | 0 275 667 | 7/1998 |
| FR | 2 565 981 | 12/1985 |
| JP | 63284177 | 11/1988 |
| JP | 4273857 | 9/1992 |
| WO | WO 86/00896 | 2/1986 |
| WO | WO 92/04343 | 3/1992 |
| WO | WO 93/12780 | 7/1993 |
| WO | WO 93/16069 | 8/1993 |
| WO | WO 93/20078 | 10/1993 |
| WO | WO 93/25546 | 12/1993 |
| WO | WO 94/14434 | 7/1994 |
| WO | WO 96/03377 | 2/1996 |
| WO | WO 96/31492 | 10/1996 |
| WO | WO 96/33171 | 10/1996 |
| WO | WO 96/37467 | 11/1996 |
| WO | WO 96/37469 | 11/1996 |
| WO | WO 97/12613 | 4/1997 |
| WO | WO 97/12615 | 4/1997 |
| WO | WO 97/30704 | 8/1997 |
| WO | WO 97/35572 | 10/1997 |
| WO | WO 98/06703 | 2/1998 |
| WO | WO 99/07351 | 2/1999 |
| WO | WO 99/07678 | 2/1999 |
| WO | WO 99/33800 | 7/1999 |

OTHER PUBLICATIONS

CA 125:142551, Elliott et al. 1996.*
CA 125:125:58312, Kitano et al. 1996.*
Krutosikova, A. et al. Synthesis and Reactions of Furo[2, 3–b]pyrroles. Molecules 2, 69–79 (1997).

(List continued on next page.)

Primary Examiner—Jane Fan
(74) Attorney, Agent, or Firm—Ropes & Grey

(57) ABSTRACT

Compounds of formula (I) or a pharmaceutically acceptable salt, in vivo hydrolysable ester, or an N—$C_{1-6}$alkyl or N,N-di-($C_{1-6}$alkyl)amide thereof, where X is $CH_2$ or $SO_2$; $R^1$ is an aryl optionally substituted by alkyl, alkenyl, alkynyl, halo, haloalkyl including perhaloalkyl such as trifluoromethyl, mercapto, alkoxy, haloalkoxy, alkenyloxy, alkynyloxy, hydroxyalkoxy, alkoxyalkoxy, alkanoyl, alkanoyloxy, cyano, nitro, amino, mono- or di-alkyl amino, oximino, sulphonamido, carbamoyl, mono or dialkylcarbamoyl or $S(O)_m R^{21}$ where m is defined above and $R^{21}$ is hydrocarbyl; $R^4$ is a group $OR^{15}$ or $S(O)_q R^{15}$, where q is 0, 1 or 2 and $R^{15}$ is a hydrogen-containing alkyl group substituted by at least one functional group as defined below, or an aryl group which is optionally substituted by one or more functional groups as defined below; and R2, R3, R5, R6 and R7 are specified organic groups. These compounds are useful in therapy, in particular of inflammatory disease, and methods of producing them as well as pharmaceutical compositions containing them are also described and claimed.

9 Claims, No Drawings

OTHER PUBLICATIONS

Yokoyama. Y. et al. Palladium–Catalyzed Cross–Coupling Reaction: Direct Allylation of Aryl Bromides with Allyl Acetate, Tetrahedron Letters 26, 6457–6460 (1985).

Berman, J.W. et al. Localization of Monocyte Chemoattractant Peptide–1 Expression in the Central Nervous System in Experimental Autoimmune Encephalomyelitis and Trauma in the Rat. *J. Immunol.* 156, 3017–3023 (1996).

Bobosik, V. & Krutosikova, A. Synthesis of N–Phenylsulfonyl Protected Furo[3,2–b]Pyrroles. *Collect. Czech. Chem. Commun.* 59, 499–502 (1994).

Dandarova, M. 13C NMR Spectra of Some Substituted Furo[3,2–b]pyrroles. *Magnetic Resonance Chem.* 28, 830–831 (1990).

Deleuran, M. et al. Localization of monocyte Chemotactic and activating factor (MCAF/MCP–1) in psoriasis. *J. Dermatological Sci.* 13, 228–236 (1996).

Grimm, M.C. et al. Enhanced expression and production of monocyte chemoattractant protein–1 in inflammatory bowel disease mucosa. *J. Leukocyte Biol.* 59, 804–812 (Jun. 1996).

Harrison, C.–A. et al. Cyclopenta [b] indoles. Part 2. Model studies towards the tremorgenic mycotoxins. *J. Chem. Soc. Perkin Trans.* 1131–1136 (1995).

Hartman, G.D. & Halczenko, W. The Synthesis of 5–Alkylaminomethylthieno[2,3–b]pyrrole–5–sulfonamides. *Heterocycles* 29, 1943–1949 (1989).

Jones, M.L. et al. Potential Role of Monocyte Chemoattractant Protein 1/JE in Monocyte/Macrophage–Dependent IgA Immune Complex Alveolitis in the Rat. *J. Immunol.* 149, 2147–2154 (Sep. 15, 1992).

Kataoka, K. et al. Homopiperazines as cell migration inhibitors. *Chemical Abstracts*, Columbus Ohio, US 123, 667 (Oct. 2, 1995).

Koch, A.E. et al. Enhanced Production of Monocyte Chemoattractant Protein–1 Rheumatoid Arthritis. *J. Clin. Invest.* 90, 772–779 (Sep. 1992).

Korobchenko, L.V. et al. Synthesis and antiviral activity of pyrrolecarboxylic acids and their derivatives. *Chemical Abstracts* Columbus, Ohio, Access No.: 119:62465 (1999).

Krutosikova, A. & Dandarova, M. Substituted Vinyl Azides in Synthesis of Furo[3,2–b:4,5–b]–Dipyrroles and Pyrrolo [2',3':4,5]Furo[3,2–c]Pyridines. *Heterocycles* 37, 1695–1700 (1994).

Krutosikova, A. & Dandarova, M. Reactions of Methyl 2–Formylfuro[3,2–b]pyrrole–5–carboxylates. *Chem. Papers* 50, 72–76 (1996).

Krutosikova, A. & Hanes, M. Substituted 4–Benzylfuro[3,2–b]Pyrroles. *Collect. Czech Chem.* 57, 1487–1494 (1992).

Krutosikova, A. et al. Condensed O–, N–Heterocycles by the Transformation of Azidoacrylates. *Chemical Monthly* 123, 807–815 (1992).

Krutosikova, A. et al. Derivatives of Furo[3,2–b]Pyrrole. *Collect. Czech. Chem. Commun.* 59, 473–481 (1994).

Krutosikova, A. et al. Substituted Vinyl Azides in the Synthesis of Condensed Nitrogen Heterocycles. *Chem. Papers* 48, 268–273 (1994).

Krutosikova, A. et al. Synthesis and Reactions of Furo[3,2–b]Pyrrole Type Aldehydes. *Collect. Czech. Chem. Commune.* 58, 2139–2149 (1993).

Murakami, Y. et al. Direct Regioselective Vinylation of Indoles Using Palladium (II) Chloride. *Heterocycles* 22, 1493–1496 (1984).

Rosenmund, P. et al. Decarboxylations of Some 1–Alkyl–2–carboxy–3–indolacetic Acids and Synthesis of a 5–Thiocyanato–2,3–dihydroindole. *Chem. Ber.* 108, 3538–3542 (1975).—Abstract only.

Troschutz, R. & Hoffmann, A. Synthesis of Substituted 3–Amino–4–cyano–1–oxo–1,2,5,10–tetrahy–droazepino[3,4–b]indoles. *J. Heterocyclic Chem.* 34, 1431 (1997).

Yokoyama, Y. et al. New Synthetic Method for Dehydrotryptophan Derivatives. Synthesis Studies on Indoles and Related Compounds. XXIV. *Chem. Pharm. Bull.* 42, 832–838 (1994).

\* cited by examiner

ANTI-INFLAMMATORY INDOLE DERIVATIVES

This application is a 371 of PCT/GB00/00275 Jan. 31, 2000 now WO 00/46198.

The present invention relates to chemical compounds, to their production as well as to pharmaceutical compositions containing them and to their use in therapy, in particular of inflammatory disease.

MCP-1 is a member of the chemokine family of proinflammatory cytokines which mediate leukocyte chemotaxis and activation. MCP-1 is a C—C chemokine which is one of the most potent and selective T-cell and monocyte chemoattractant and activating agents known. MCP-1 has been implicated in the pathophysiology of a large number of inflammatory diseases including rheumatoid arthritis, glomerular nephritides, lung fibrosis, restenosis (International Patent Application WO 94/09128), alveolitis (Jones et al., 1992, *J. Immunol.*, 149, 2147) and asthma. Other disease areas where MCP-1 is thought to play a part in their pathology are atherosclerosis (e.g. Koch et al., 1992, *J. Clin. Invest.*, 90, 772–779), psoriasis (Deleuran et al., 1996, *J. Dermatological Science*, 13,. 228–236), delayed-type hypersensitivity reactions of the skin, inflammatory bowel disease (Grimm et al., 1996, *J. Leukocyte Biol.*, 59,. 804–812), multiple sclerosis and brain trauma (Berman et al, 1996, *J. Immunol.*, 156,. 3017–3023). An MCP-1 inhibitor may also be useful to treat stroke, reperfusion injury, ischemia, myocardial infarction and transplant rejection.

MCP-1 acts through the MCP-1 receptor (also known as the CCR2 receptor). MCP-2 and MCP-3 may also act, at least in part, through the MCP-1 receptor. Therefore in this specification, when reference is made to "inhibition or antagonism of MCP-1" or "MCP-1 mediated effects" this includes inhibition or antagonism of MCP-2 and/or MCP-3 mediated effects when MCP-2 and/or MCP-3 are acting through the MCP-1 receptor.

Copending International Patent Application Nos. PCT/GB98/02340 and PCT/GB98/02341 describe and claim groups of compounds based upon the indole ring structure which are inhibitors of MCP-1 and therefore have applications in therapy.

The use of certain indole derivatives as NMDA antagonists is described is U.S. Pat. No. 5,051,442, WO 9312780, EP-483881. Other indoles and their use as inhibitors of leukotriene biosynthesis is described in for example, EP-A-275-667, EP-A-419049 and U.S. Pat. No. 5,190,968.

More recently, WO 99/33800 describes various indole derivatives as inhibitors of factor XA.

The applicants have found a particular substitution at the 4-position on the indole ring produces advantageous results when used therapeutically as inhibitors of MCP-1.

According to the present invention there is provided a compound of formula (I)

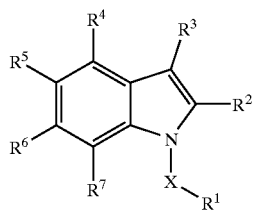

(I)

where:

X is CH$_2$, or SO$_2$

R$^1$ is an optionally substituted aryl or heteroaryl ring;

R$^2$ is carboxy, cyano, —C(O)CH$_2$OH, —CONHR$^8$, —SO$_2$NHR$^8$, tetrazol-5-yl, SO$_3$H, or a group of formula (VI)

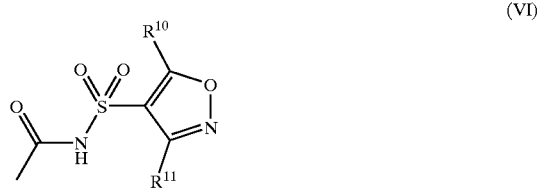

(VI)

where R$^8$ is selected from hydrogen, alkyl, aryl, cyano, hydroxy, —SO$_2$R$^{12}$ where R$^{12}$ is alkyl, aryl, heteroaryl, or haloalkyl, or R$^8$ is a group-(CHR$^{13}$)$_r$—COOH where r is an integer of 1–3 and each R$^{13}$ group is independently selected from hydrogen or alkyl; R$^9$ is hydrogen, alkyl, optionally substituted aryl such as optionally substituted phenyl or optionally subtituted heteroaryl such as 5 or 6 membered heteroaryl groups, or a group COR$^{14}$ where R$^{14}$ is alkyl, aryl, heteroaryl or haloalkyl; R$^{10}$ and R$^{11}$ are independently selected from hydrogen or alkyl, particularly C$_{1-4}$ alkyl;

R$^3$ is hydrogen, a functional group, optionally substituted alkyl, optionally substituted alkenyl, optionally substituted alkynyl, optionally substituted aryl, optionally substituted heterocyclyl, optionally substituted alkoxy, optionally substituted aralkyl, optionally substituted aralkyloxy, optionally substituted cycloalkyl;

R$^4$ is a group OR$^{15}$ or S(O)$_q$R$^{15}$, where q is 0, 1 or 2 and R$^{15}$ is a substituted hydrogen-containing alkyl group; and R$^5$, R$^6$ and R$^7$ are independently selected from hydrogen, a functional group or an optionally substituted hydrocarbyl group or optionally substituted heterocyclic group.

Suitably, R$^4$ is other than a OR$^{15}$ where R$^{15}$ is C$_{1-4}$alkyl substituted a single unsubstituted phenyl, such as benzyloxy.

In addition, the invention provides a pharmaceutically acceptable salt, in vivo hydrolysable ester, or amide of the compound of formula (I).

Compounds of formula (I) are inhibitors of monocyte chemoattractant protein-1. In addition, they appear to inhibit RANTES induced chemotaxis. RANTES is another chemokine from the same family as MCP-1, with a similar biological profile, but acting though the CCR1 receptor. As a result, these compounds can be used to treat disease mediated by these agents, in particular inflammatory disease. Thus the invention further provides a compound of formula (I) for use in the treatment of inflammatory disease.

In this specification the term 'alkyl' when used either alone or as a suffix includes straight chained, branched structures. These groups may contain up to 10, preferably up to 6 and more preferably up to 4 carbon atoms. Similarly the terms "alkenyl" and "alkynyl" refer to unsaturated straight or branched structures containing for example from 2 to 10, preferably from 2 to 6 carbon atoms. Cyclic moieties such as cycloalkyl, cycloalkenyl and cycloalkynyl are similar in nature but have at least 3 carbon atoms. Terms such as "alkoxy" comprise alkyl groups as is understood in the art.

When it is stated that the an alkyl group is "hydrogen containing", it means that at least one hydrogen atom is present, thus excluding perhaloalkyl groups for example.

The term "halo" includes fluoro, chloro, bromo and iodo. References to aryl groups include aromatic carbocylic groups such as phenyl and naphthyl. The term "heterocyclyl" includes aromatic or non-aromatic rings, for example containing from 4 to 20, suitably from 5 to 8 ring atoms, at least one of which is a heteroatom such as oxygen, sulphur or nitrogen. Examples of such groups include furyl, thienyl, pyrrolyl, pyrrolidinyl, imidazolyl, triazolyl, thiazolyl, tetrazolyl, oxazolyl, isoxazolyl, pyrazolyl, pyridyl, pyrimidinyl, pyrazinyl, pyridazinyl, triazinyl, quinolinyl, isoquinolinyl, quinoxalinyl benzothiazolyl, bernzoxazolyl, benzothienyl or benzofuryl.

"Heteroaryl" refers to those groups described above which have an aromatic character. The term "aralkyl" refers to aryl substituted alkyl groups such as benzyl.

Other expressions used in the specification include "hydrocarbyl" which refers to any structure comprising carbon and hydrogen atoms. For example, these may be alkyl, alkenyl, alkynyl, aryl, heterocyclyl, alkoxy, aralkyl, cycloalkyl, cycloalkenyl or cycloalkynyl.

The term "functional group" refers to reactive substituents. They may comprise electron-donating or electron-withdrawing. Examples of such groups include halo, cyano, nitro, $C(O)_nR^{18}$, $OR^{18}$, $S(O)_mR^{18}$, $NR^{19}R^{20}$, $C(O)NR^{19}R^{20}$, $OC(O)NR^{19}R^{20}$, $-NR^{19}C(O)_nR^{18}$, $-NR^{18}CONR^{19}R^{20}$, $-N=CR^{18}R^{19}$, $S(O)_nNR^{19}R^{20}$ or $-NR^{19}S(O)_mR^{18}$ where $R^{18}$, $R^{19}$ and $R^{20}$ are independently selected from hydrogen or optionally substituted hydrocarbyl, or $R^{19}$ and $R^{20}$ together form an optionally substituted heterocyclic ring as defined above, which optionally contains further heteroatoms such as sulphur, S(O), $SO_2$, oxygen and nitrogen, n is an integer of 1 or 2, m is an integer of 1–3.

Suitable optional substituents for hydrocarbyl groups $R^{18}$, $R^{19}$ and $R^{20}$ include halo, perhaloalkyl such as trifluoromethyl, mercapto, hydroxy, carboxy, alkoxy, heteroaryl, heteroaryloxy, alkenyloxy, alkynyloxy, alkoxyalkoxy, aryloxy (where the aryl group may be substituted by halo, nitro, or hydroxy), cyano, nitro, amino, mono- or di-alkyl amino, oximino or $S(O)_{m'}R^{16}$ where m' is 1 or 2 and $R^{16}$ is alkyl.

Where $R^{19}$ and $R^{20}$ form a heterocyclic group, this may be optionally substituted by hydrocarbyl such as alkyl as well as those substituents listed above for hydrocarbyl groups.

Suitable substituents for hydrocarbyl or heterocylic groups $R^5$, $R^6$ and $R^7$ include those listed above for $R^{18}$, $R^{19}$ and $R^{20}$.

Suitably $R^1$ is an optionally substituted phenyl, pyridyl, naphthyl, furyl or thienyl ring, and in particular is a substituted phenyl or pyridyl ring.

Suitable optional substitutents for $R^1$ in formula (I) include alkyl, alkenyl, alkynyl, halo, haloalkyl including perhaloalkyl such as trifluoromethyl, mercapto, alkoxy, haloalkoxy, alkenyloxy, alkynyloxy, hydroxyalkoxy, alkoxyalkoxy, alkanoyl, alkanoyloxy, cyano, nitro, amino, mono- or di-alkyl amino, oximino, sulphonamido, carbamoyl, mono or dialkylcarbamoyl or $S(O)_mR^{21}$ where m is as defined above and $R^{21}$ is hydrocarbyl.

Particular examples of substituents $R^5$, $R^6$ and $R^7$ include hydrogen, hydroxy, halo, optionally substituted alkyl such as aralkyl, carboxyalkyl or the amide derivative thereof; alkoxy; aryloxy; aralkyloxy; or an amino group which is optionally substituted with alkyl, aryl or aralkyl. A specific functional group which is suitable for $R^5$, $R^6$ and/or $R^7$ is a group of sub-formula (IV).

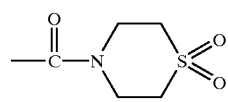

(IV)

Particular examples of groups $R^5$, $R^6$ and $R^7$ are hydrogen, hydroxy, halo or alkoxy. In particular $R^6$ and $R^7$ are hydrogen. $R^5$ may be hydrogen but in addition is suitably a small subsitutent such as hydroxy, halo or methoxy.

Particular substituents for $R^1$ include trifluoromethyl, $C_{1-4}$alkyl, halo, trifluoromethoxy, $C_{1-4}$alkoxy, $C_{1-4}$alkanoyl, $C_{1-4}$alkanoyloxy, nitro, carbamoyl, $C_{1-4}$alkoxycarbonyl, $C_{1-4}$alkylsulphanyl, $C_{1-4}$alkylsulphinyl, $C_{1-4}$alkylsulphonyl, sulphonamido, carbamoyl$C_{1-4}$alkyl, N-($C_{1-4}$alkyl) carbamoyl$C_{1-4}$alkyl, N-($C_{1-4}$alkyl)$_2$carbamoyl-$C_{1-4}$alkyl, hydroxy$C_{1-4}$alkyl or $C_{1-4}$alkoxy$C_{1-4}$alkyl.

Additionally or alternatively, two such substituents together may form a divalent radical of the formula $-O(CH_2)_{1-4}O-$ attached to adjacent carbon atoms on the $R^1$ ring.

Preferred substitutents for $R^1$ are one or more non-polar substituents such as halo.

In particular, $R^1$ is substituted by one or more halo groups, in particular chlorine. A particular example of an $R^1$ group is 3,4-dichlorophenyl, 3-fluoro-4-chlorophenyl, 3-chloro-4-fluorophenyl or 2,3-dichloropyrid-5-yl.

Examples of groups $R^2$ include carboxy; cyano; tetrazol-5-yl; $SO_3H$; $-CONHR^8$ where $R^8$ is selected from cyano, hydroxy, $-SO_2R^{12}$ where $R^{12}$ is alkyl such as $C_{1-4}$ alkyl, aryl such as phenyl, heteroaryl or trifluoromethyl, or $R^8$ is a group-$(CHR^{13})_r$-COOH where r is an integer of 1–3 and each $R^{13}$ group is independently selected from hydrogen or alkyl such as $C_{1-4}$ alkyl; or $R^2$ is a group $-SO_2NHR^9$ where $R^9$ is an optionally substituted phenyl or an optionally substituted 5 or 6 membered heteroaryl group, or a group $COR^{14}$ where $R^{14}$ is alkyl such as $C_{1-4}$ alkyl, aryl such as phenyl, heteroaryl or trifluormethyl, or $R^2$ is a group of formula (VI)

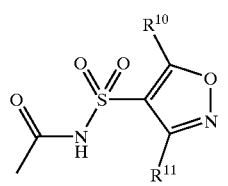

(VI)

where $R^{10}$ and $R^{11}$ are independently selected from hydrogen or alkyl, particularly $C_{1-4}$ alkyl.

Preferably $R^2$ is carboxy or a pharmaceutically acceptable salt or ester thereof.

Suitable groups $R^3$ include hydrogen, fluoro, chloro, bromo, iodo, methyl, cyano, trifluoromethyl, hydroxymethyl, alkoxyalkyl such as $C_{1-4}$alkoxymethyl, methoxy, benzyloxy, carboxyalkoxy such as carboxymethoxy, methylsulphanyl, methylsulphinyl, methylsulphonyl or carboxy$C_{3-6}$cycloalkyl, $-(CHR^{22})_r-$ $NR^{23}R^{24}$ (where r is 0–2, each $R^{22}$ is independently hydrogen or alkyl, in particular $C_{1-4}$ alkyl, $R^{23}$ and $R^{24}$ are independently selected from H and $C_{1-4}$alkyl or $R^{23}$ and $R^{24}$ together with the nitrogen to which they are attached form a 5 or 6 membered ring optionally containing one further heteroatom selected from O, N, S, S(O) or $SO_2$. Suitably $R^{23}$ and $R^{24}$ together form a heterocylic ring such as morpholino or piperazinyl.

Other such groups $R^3$ include optionally substituted aryl groups, such as optionally substituted phenyl or naphthyl group. Suitable substituents for phenyl groups $R^3$ include one or more groups selected from chlorine, fluorine, methyl, trifluoromethyl, trifluoromethoxy, amino, formyl, phenyl, methoxy, phenoxy or phenyl.

$R^3$ may comprise a range of substituents as listed above, in particular, hydrogen or a small substituent group such as $C_{1-4}$alkyl in particular methyl, or trifluoromethyl, and is preferably hydrogen.

Suitably $R^{15}$ as used in the definition of $R^4$ comprises a $C_{1-3}$alkyl group.

Suitable optional substitutents for the group $R^{15}$ include one or more groups selected from functional groups as hereinbefore defined, as well as aryl or heterocyclyl groups, either of which may themselves be substituted by one or more functional groups. Preferably, when $R^{15}$ is an aryl group such as phenyl, the phenyl ring is substituted by for example, a functional group. Preferably, when $R^{15}$ has a heteroaryl substituent, it is spaced from the indole ring by more than one $CH_2$ group, and so the alkyl group $R^{15}$ is other than methyl. Most preferably, when $R^{15}$ has a heterocyclic substituent, it is non-aromatic, such as morpholino, tetrahydropyrazinyl where the second nitrogen atom is H, alkyl or hydroxy alkyl substituted, (and in particular is H or alkyl substituted) or a group

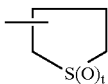

where t is 0,1 or 2 and preferably 2.

Suitable substitutents for $C_{1-3}$ alkyl groups $R^{15}$ are with one or more groups selected from halo; hydroxy; cyano; amino, mono- or di-alkylamino wherein each alkyl group is optionally substituted by hydroxy, alkoxy or heterocyclyl; $C_{1-4}$ alkoxy; carboxy; sulphonamido; $CONH_2$; morpholino; tetrahydropyrazinyl which is optionally N-substituted by alkyl or hydroxyalkyl; tetrahydropyridyl optionally substituted by hydroxy or hydroxyalkyl, pyridyl, pyrimidinyl, phenyl optionally substituted by carboxy, halo, hydroxy, alkoxy, carbamoyl, acyl or hydroxyalkyl where the alkyl group suitably includes at least two carbon atoms.

Preferably, when $R^{15}$ is alkyl substituted by phenyl, either the alkyl moiety carries a further substituent as described above, or the phenyl ring is substituted as described above.

Particular examples of substituents for groups $R^{15}$ as present in $R^4$ include one or more groups selected from halo such as chloro, hydroxy, cyano, amino, mono- or di-alkylamino, $C_{1-4}$ alkoxy, carboxy, sulphonamido, $CONH_2$, morpholino, tetrahydropyrazinyl which is optionally N-substituted by alkyl or hydroxy alkyl, pyridyl, pyrimidinyl, phenyl optionally substituted by carboxy, halo such as chloro, hydroxy, alkoxy such as methoxy, carbamoyl, acyl such as acetyl, or hydroxyalkyl where the alkyl group suitably includes at least two carbon atoms, such as hydroxyethyl.

Where $R^{15}$ is a heterocyclic group, these may be substituted by functional groups, or by alkyl groups such as methyl or ethyl, or alkenyl or alkynyl groups any of which may be subsituted, for example with hydroxy.

A preferred group for $R^4$ is a group $OR^{15}$ where $R^{15}$ is a straight or branched chain alkyl group which carries at least one hydroxy group, for example 1 or 2 hydroxy groups. Other substituents, as defined above, may be provided on the alkyl chain.

Preferably $R^{15}$ is a group of formula $-(CH_2)_a[(CHOH)(CH_2)_b]_d CH_2OH$ where a is an integer of from 1 to 4, b is 0 or an integer of from 1 to 4, and d is 0 or 1.

Examples of such $R_{15}$ include $CH_2CHOHCH_2OH$ and $CH_2CH_2OH$, $CH_2CH_2CH_2OH$, X is $C_2$ or $SO_2$ and is preferably $CH_2$.

Suitable pharmaceutically acceptable salts of compounds of formula (I) include are base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or amino acids for example lysine. In another aspect, where the compound is sufficiently basic, suitable salts include acid addition salts such as methanesulfonate, fumarate, hydrochloride, hydrobromide, citrate, maleate and salts formed with phosphoric and sulphuric acid. There may be more than one cation or anion depending on the number of charged functions and the valency of the cations or anions. A preferred pharmaceutically acceptable salt is a sodium salt.

An in vivo hydrolysable ester of a compound of the formula (I) containing carboxy or hydroxy group is, for example, a pharmaceutically acceptable ester which is hydrolysed in the human or animal body to produce the parent acid or alcohol.

Suitable pharmaceutically acceptable esters for carboxy include $C_{1-6}$alkyl esters such as methyl or ethyl esters, $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

Suitable amides include, for example, a $N-C_{1-6}$alkyl and $N,N$-di-$(C_{1-6}$alkyl)amide such as N-methyl, N-ethyl, N-propyl, N,N-dimethyl, N-ethyl-N-methyl or N,N-diethylamide.

Esters which are not in vivo hydrolysable are useful as intermediates in the production compounds of formula (I) and therefore these form a further aspect of the invention.

Thus examples of compounds of formula (I) include the following:

TABLE 1

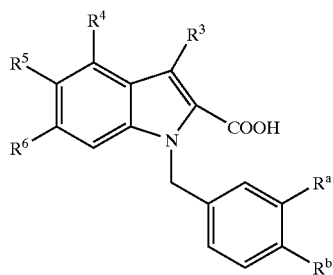

| Compd No. | R³ | R⁴ | R⁵ | R⁶ | Rᵃ | Rᵇ |
|---|---|---|---|---|---|---|
| 1 | H | OCH₂CH₂OH | H | H | H | H |
| 2 | H | OCH₂CH₂OCH₃ | H | H | H | H |
| 3 | H | *-O-(CH₂)₃-morpholinyl | H | H | H | H |
| 4 | H | *-O-(CH₂)₃-(4-methylpiperazinyl) | H | H | H | H |
| 5 | H | OCH₂COOH | H | H | F | F |
| 6 | H | OCH₂COOH | H | H | Cl | H |
| 7 | H | *-O-CH(COOH)-phenyl | H | H | H | H |
| 8 | H | OCH₂COOH | H | H | H | Cl |
| 9 | H | OCH₂COOH | OCH₃ | H | Cl | Cl |
| 10 | H | *-O-(CH₂)₃-morpholinyl | OCH₃ | H | Cl | Cl |
| 11 | H | OCH₂CONH₂ | OCH₃ | H | Cl | Cl |
| 12 | H | OCH(CH₃)COOH | H | H | Cl | Cl |
| 13 | H | *-O-CH₂-(3-methoxy-4-carboxyphenyl) (see structure) | H | H | Cl | Cl |
| 14 | H | O(CH₂)₂OH | H | H | Cl | Cl |
| 15 | H | O(CH₂)₃OH | H | H | Cl | Cl |
| 16 | H | OCH₂CH(OH)CH₂N(CH₃)₂ | H | H | Cl | Cl |
| 17 | H | *-OCH₂CH(OH)CH₂-morpholinyl | H | H | Cl | Cl |

TABLE 1-continued

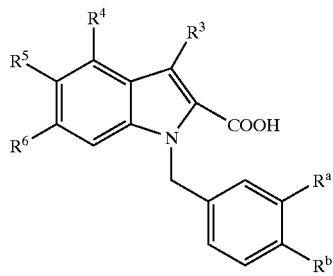

| Compd No. | R³ | R⁴ | R⁵ | R⁶ | Rᵃ | Rᵇ |
|---|---|---|---|---|---|---|
| 18 | H | O(CH₂)₂N(CH₃)₂ | H | H | Cl | Cl |
| 19 | H | S(CH₂)₃OH | H | H | Cl | Cl |
| 20 | H | S(O)₂(CH₂)₃OH | H | H | Cl | Cl |
| 21 | H | OCH₂CHOHCH₂OH | H | H | Cl | Cl |
| 22 | H | *—O—CH₂CH₂—N(piperazine)N—CH₂CH₂OH | H | H | Cl | Cl |
| 23 | H | *—O—CH₂—CH(OH)—CH₂—NH—(cyclohexyl-4-OH) | H | H | Cl | Cl |
| 24 | H | *—O—CH₂—CH(OH)—CH₂—NH—CH₂CH₂—(morpholine) | H | H | Cl | Cl |
| 25 | H | *—O—CH₂—CH(OH)—CH₂—N(piperidine-4-OH) | H | H | Cl | Cl |
| 26 | H | *—O—CH₂—CH(OH)—CH₂—N(CH₂CH₂OCH₃)₂ | H | H | Cl | Cl |
| 27 | H | *—O—CH₂—CH(OH)—CH₂—N(CH₃)—CH₂—(tetrahydrofuran-2-yl) | H | H | Cl | Cl |
| 28 | H | *—O—CH₂—CH(OH)—CH₂—N(CH₃)—CH₂CH₂OH | H | H | Cl | Cl | where * indicates the point of attachment of the group to the indole ring.

Compounds of formula (I) are suitably prepared by methods such methods analogous to those described in International Patent Application Nos. PCT/GB98/02340 and PCT/GB98/02341.

In particular compounds of formula (I) can be prepared by reacting a compound of formula (VII)

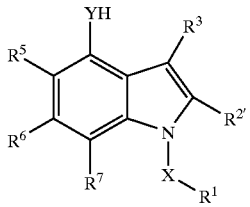

(VII)

where $R^1$, $R^3$, $R^5$, $R^6$, $R^7$ and X are as defined in relation to formula (I), $R^{2'}$ is a group $R^2$ as defined in relation to formula (I) or a protected form thereof and Y is oxygen or sulphur with a compound of formula (VIII)

(VIII)

where Z is a leaving group and $R^{15'}$ is a group $R^{15}$ as defined in claim 1 or a precursor thereof, and thereafter if desired or necessary carrying out one or more of the following steps:

(i) converting a precursor group $R^{15'}$ to a group $R^{15}$;
(ii) converting a group $R^{15}$ to another such group:
(iii) oxidising a thiol group $R^4$ to a sulphinyl or sulphonyl group;
(iv) deprotecting a group $R^{2'}$ or converting the existing group $R^2$ to a different $R^2$ group.

The reaction between the compounds of formula (VII) and (VIII) is suitably effected in an organic solvent such as dimethylformamide (DMF) in the presence of a base such as a hydride or carbonate salt, in particular sodium hydride or potassium carbonate. Temperatures in the range of from 0° to 100° C. are suitably employed. Examples of suitable leaving groups Z include halogen such as chloro and bromo.

In general, the compound of formula (VII) will comprise a compound where $R^{2'}$ is an ester group. Deesterification in optional step (iv) using conventional methods as illustrated hereinafter will yield the corresponding compound of formula (I) where $R^2$ is a carboxylic acid group.

Optional step (i) above may be carried out using conventional methods, depending upon the precise nature of the precursor involved. For example, a precursor to a di-substituted alkyl group $R^{15}$ may be an epoxide. Addition of an amine to the expoxide, for example as illustrated hereinafter will result in the production of a compound of formula (I) where $R^{15}$ carries both a hydroxy and an amine substituent. Many other possible reactions of this nature would be apparent to a chemist.

Similarly, optional step (ii) may be effected using conventional methods. For example, halo substituents may be replaced by others using a nucleophilic displacement reaction. Again, examples of such reactions are given hereinafter, but many others would be readily apparent.

Oxidation in optional step (iii) is suitably effected using an appropriate oxidising agent. For instance hydrogen peroxide may be reacted with a thiol to produce the corresponding sulphonyl compound of formula (I).

Compounds of formula (VII) can be prepared in various ways depending upon the nature of the group Y. For instance, when Y is oxygen, the compound of formula (VII) may be prepared by reacting a compound of formula (IX)

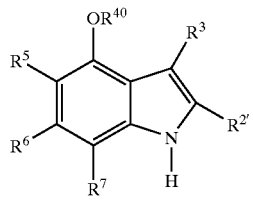

(IX)

where $R^3$, $R^5$, $R^6$ and $R^7$ are as defined in relation to formula (I), $R^{2'}$ is as defined in relation to formula (VII) and $R^{40}$ is a protecting group such as acetyl or benzyl; with compound of formula (X)

(X)

where $R^1$ and X are as defined in relation to formula (I) and $Z^1$ is a leaving group, and thereafter removing the protecting group $R^{40}$.

Suitable leaving groups for Z include halide such as chloride, bromide or iodide, as well as mesylate or tosylate. The reaction is suitably effected in an organic solvent such as dimethylformamide (DMF) tetralydrofuran (THF) or DCM in the presence of a base such as sodium hydride, sodium hydroxide, potassium carbonate. Optionally the reaction is effected in the presence of a suitable phase transfer catalyst. The choice of base and solvent is interdependent to a certain extent in that certain solvents are compatible with some bases only as is understood in the art. For example, sodium hydride may preferably be used with dimethylformamide or tetrahydrofuran and sodium hydroxide is preferably used with dichloromethane and a phase transfer catalyst.

The reaction can be carried out at moderate temperatures, for example from 0 to 50° C. and conveniently at about ambient temperature.

Preferably, $R^{2'}$ is an ester group in the compound of formula IX and this may be subsequently converted to an acid or to another ester or salt, by conventional methods later in the process. For example, when X is a group $SO_2$ and $R^2$ is a methyl ester of carboxy, it may be converted to the corresponding carboxylic acid by reaction with lithium iodide in dry pyridine or DMF.

The reaction conditions employed in the deprotection step to remove $R^{40}$ will depend upon the nature of the protecting group $R^{40}$ and would be apparent to a skilled person. Acetyl groups may be removed by reaction with a strong base such as sodium methoxide, whereas benzyl groups may be removed by hydrogenation, for example in the presence of a palladium catalyst.

Compounds of formula (IX) may be prepared by cyclisation of a compound of formula (XII)

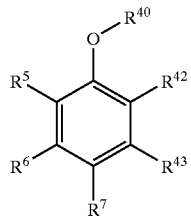

(XII)

where $R^5$, $R^6$, $R^7$ and $R^{40}$ are as defined above and $R^{42}$ and $R^{43}$ represent a combination of moieties which can cyclise to form an appropriately substituted pyrrole ring. For example, $R^{42}$ can be a group of formula —CH=C($R^{44}$)$N_3$ where $R^{44}$ is a group $R^2$ as defined above, or a protected form thereof, and $R^{43}$ may be hydrogen. Cyclisation to form a compound of formula (XII) may then be effected by heating for example under reflux in an organic solvent, in particular a high boiling aprotic solvent such as xylene or toluene.

Alternatively, $R^{43}$ may be nitro and $R^{42}$ may be a group of formula —$CH_2C(O)R^{2'}$ where $R^{2'}$ is as defined above in relation to formula (VII). These compounds will cyclise in the presence of a catalyst such as palladium on carbon in the presence of hydrogen. The reaction may be effected at moderate temperatures for example of from 0 to 80° C., conveniently at about ambient temperature.

Thus examples of compounds of formula (XII) include compounds of formula (XIII) and (XIV)

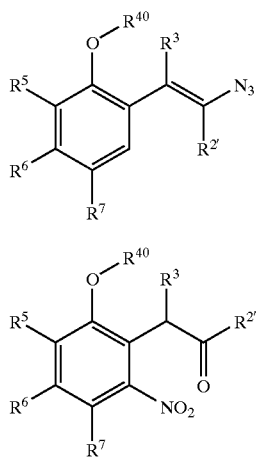

(XIII)

(XIV)

where $R^{2'}$, $R^3$, $R^5$, $R^6$, $R^7$ and $R^{40}$ are as defined above.

Compounds of formula (XIII) where $R^3$ is hydrogen may be prepared for example by reacting a compound of formula (XV)

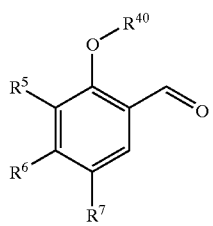

(XV)

with a compound of formula (XVI)

$N_3CH_2R^{2'}$ (XVI)

where $R^5$, $R^6$, $R^7$ and $R^{2'}$ are as defined hereinbefore. The reaction may be effected in an organic solvent such as ethanol at low temperatures of from −20 to 0° C., suitably at about 0° C. The reaction is suitably effected in the presence of a base such as an alkoxide, in particular an ethoxide, for example potassium ethoxide.

Where necessary or desired, a group $R^3$ which is other than hydrogen may be added using conventional methods, later in the process.

Compounds of formula (XVI) are suitably prepared by reacting a compound of formula (XVII)

$R^{47}CH_2R^{2'}$ (XVII)

where $R^{2'}$ is as defined above and $R^{47}$ is a leaving group such as halide and in particular bromide, with an azide salt, such as an alkali metal azide salt in particular sodium azide.

Compounds of formula (XIV) may be prepared by reacting a compound of formula (XVIII)

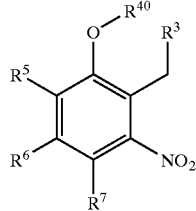

(XVIII)

where $R^5$, $R^6$, $R^7$, $R^3$ and $R^{40}$ are as defined above, with a compound of formula (XIX)

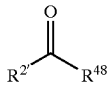

(XIX)

where $R^{2'}$ is as defined above and $R^{48}$ is a leaving group such as alkoxy. Examples of compounds of formula (XIX) are oxalates such as diethyloxalate. The reaction is suitably effected in the presence of a base such as sodium hydride in an organic solvent such as THF. Moderate temperatures of from 0° to 40° C. and conveniently ambient temperature is employed.

Compounds of formula (VII) where Y is sulphur may conveniently be prepared using alternative methods. For example, they may be prepared by reacting a compound of formula (XX)

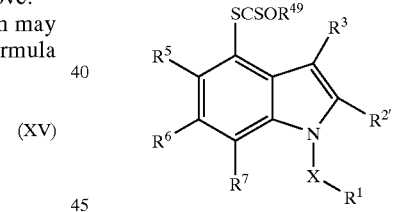

(XX)

where $R^1$, $R^3$, $R^5$, $R^6$, $R^7$ and $R^{2'}$ are as defined above and $R^{49}$ is an alkyl croup such as ethyl, with an amine such as ethylene diamine. The reaction is suitably effected in a solvent such as tetrahydrofuran at moderate temperatures from example from 0° to 50° C., conveniently at ambient temperature.

Compounds of formula (XX) are suitably derived from a compound of formula (XXI)

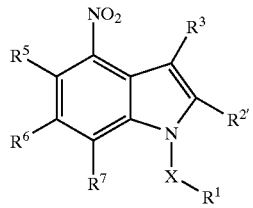

(XXI)

where $R^1$, $R^3$, $R^5$, $R^6$, $R^7$ and $R^{2'}$ are as defined above, by a sequence of reactions involving for example, the converion of the nitro group to an amino group, then to a diazonium group and subsequently to a xanthyl group. Suitable reaction conditions for these steps would be apparent from the literature and are illustrated hereinafter.

Compounds of formula (XXI) are suitably formed by reacting a compound of formula (XXII)

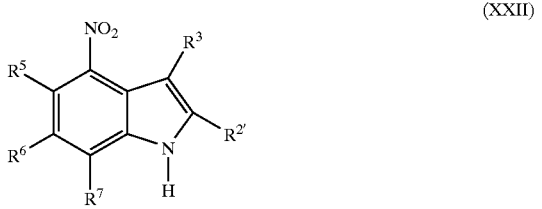

(XXII)

with a compound of formula (X) as defined above using conditions similar to those described for the reaction of compound (IX) with compound (X).

Compounds of formula (X), (XV), (XVI), (XVII), (XVIII), (XIX) and (XXII) are either known compounds or they can be prepared from known compounds by conventional methods.

According to a further aspect of the invention there is provided a compound of the formula (I) as defined herein, or a pharmaceutically acceptable salt or an in vivo hydrolysable ester thereof, for use in a method of treatment of the human or animal body by therapy. In particular, the compounds are used in methods of treatment of inflammatory disease.

According to a further aspect of the present invention there is provided a method for antagonising an MCP-1 mediated effect in a warm blooded animal, such as man, in need of such treatment, which comprises administering to said animal an effective amount of a compound of formula (I), or a pharmaceutically acceptable salt, or an in vivo hydrolysable ester thereof.

The invention also provides a pharmaceutical composition comprising a compound of formula (I) as defined herein, or a pharmaceutically acceptable salt, or an in vivo hydrolysable ester thereof, in combination with at pharmaceutically acceptable carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal track, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, $30\mu$ or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula I will naturally vary according to the nature and severity of the conditions, the age and sex of the animal or patient and the route of administration, according to well known principles of medicine. As mentioned above, compounds of the Formula I are useful in treating diseases or medical conditions which are due alone or in part to the effects of farnesylation of rats.

In using a compound of the Formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

A further aspect of the invention comprises a compound of formula (I) as defined above, or a pharmaceutically acceptable salt or in vivo hydrolysable ester thereof, for use in the preparation of a medicament for the treatment of inflammatory disease.

The invention is further illustrated, but not limited by the following Examples in which the following general procedures were used unless stated otherwise.

PREPARATION 1

Ethyl N-(3,4-dichlorobenzyl)-4-nitroindole-2-carboxylate

Ethyl 4-nitroindole-2-carboxylate (26 g) [prepared according to S. M. Parmerter el. al. *J. Amer. Chem. Soc.*, 1958, 80, 4621], 3,4-dichlorobenzyl chloride (16 ml), potassium carbonate (17 g) and potassium iodide (2 g) in DMF (250 ml) were stirred at 60° C. for 2 hours. The reaction was concentrated in vacuo and the residue partitioned between water and dichloromethane. Iso-hexane was added to the combined organic extracts resulting in crystallisation of the product as yellow needles (39 g. 89%) NMR d ($CD_3SOCD_3$) 1.30 (t, 3H), 4.32 (q, 2H), 5.93 (s, 2H), 6.88 (dd, 1H), 7.18 (d, 1H), 7.52 (d, 1H), 7.56 (dd, 1H), 7.78 (s, 1H), 8.17 (m, 2H); M/z (+) 395 ($MH^+$), 393.

PREPARATION 2

Ethyl N-(3,4-Dichlorobenzyl)-4-aminoindole-2-carboxlate

A solution of ethyl N-(3,4-dichlorobenzyl)-4-nitroindole-2-carboxylate (2.41 g) in tetrahydrofuran (100 ml) was stirred in the presence of titanium trichloride (15% aqueous solution, 50 ml) at room temperature overnight. The reaction was treated with 40% sodium hydroxide solution and extracted with 5% methanol in dichloromethane. Combined organic extracts were dried ($MgSO_4$) and concentrated in vacuo to give the product as a brown solid (1.98 g, 89%); NMR d ($CD_3SOCD_3$) 1.3 (t, 3H), 4.2 (q, 2H), 5.7 (s, 4H), 6.2 (d, 1H), 6.6 (d, 1H), 7.0 (m, 1H), 7.25 (m, 1H), 7.5 (d, 1H), 7.6 (m, 1H): M/z (+) 363.3 ($MH^+$).

PREPARATION 3

N-(3,4-Dichlorobenzyl)-2-ethoxycarbonylindole-4-diazonium Tetrafluoroborate

Ethyl N-(3,4-dichlorobenzyl)-4-aminoindole-2-carboxylate (1.98 g) was stirred in water (38 ml) and HCl (2M, 15 ml) at 0° C. and a solution of sodium nitrite (940 mg) in water (20 ml) was added dropwise over 10 minutes. This was followed by the addition of concentrated HCl (15 ml). The reaction was stirred for 1 hour at 0° C. and a saturated solution of sodium tetrafluoroborate (12 ml) was added. The resulting precipitate was collected by filtration, washed with water and dried in vacuo over phosphorous pentoxide to give the product as a light brown solid (2.51 g, 100%); NMR d (CD$_3$SOCD$_3$) 1.3 (t, 3H), 4.4 (q, 2H), 6.0 (s, 2H), 6.95 (m, 1H), 7.3 (m, 1H), 7.5 (d, 1H), 7.8 (t, 1H), 8.0 (m, 1H), 8.7 (m, 2H); M/z (+) 348.6 [M-N$_2$,BF$_4$$^+$].

PREPARATION 4

Ethyl S-[N-(3,4-Dichlorobenzyl-2-ethoxycarbonylindol-4-yl]dithiocarbamate

N-(3,4-dichlorobenzyl)-2-ethoxycarbonylindole-4-diazonium tetrafluoroborate (2.5g) was added portionwise over 10 minutes to a stirred solution of potassium ethyl xanthate (0.96 g) in acetone (60 ml) under argon at 0° C. The reaction mixture was allowed to warm to room temperature, poured into 50% brine (200 ml) and extracted with ethyl acetate. Combined organic extracts were dried (MgSO$_4$), concentrated in vacuo and the residue purified by column chromatography using iso-hexane: 5% ethyl acetate to 15% ethyl acetate as eluent to give the product as a pale yellow oil (1 g 39%): NMR d (CD$_3$SOCD$_3$) 1.1 (t, 3H), 1.3 (t, 3H), 4.3 (q, 2H), 4.55 (q, 2H), 5.9 (s, 2H), 6.9 (m, 1H), 7.4 (m, 4H), 7.5 (m, 1H), 7.8 (d, 1H); M/z (+) 468.3 (MH$^+$).

PREPARATION 5

Ethyl N-(3,4-Dichlorobenzyl)-4-mercaptoindole-2-carboxylate

Ethylene diamine (0.12 ml) was added to a solution of ethyl S-[N-(3,4-dichlorobenzy-2-ethoxycarbonylindol-4-yl]dithiocarbamate (730 mg) in tetrahydrofuran (25 ml) and stirring was continued for 16 hours. The reaction mixture was concentrated in vacuo and the residue partitioned between water and dichloromethane. Combined organic extracts were dried (MgSO$_4$) and concentrated in vacuo and the residue purified by column chromatography using iso-hexane: 10% ethyl acetate to 20% ethyl acetate as eluent to give the product as a pale yellow oil (400 mg, 67%); NMR d (CD$_3$SOCD$_3$) 1.25 (t, 3H), 4.3 (q, 2H), 5.8 (s, 2H), 6.85 (m, 1H), 7.25 (s, 1H), 7.3 (m, 2H), 7.4 (m, 1H), 7.5 (d, 1H), 7.6 (d, 1H); M/z (+) 379 (MH$^-$).

PREPARATION 6

2-Benzyloxy-3-methoxybenzaldehyde

Benzyl bromide (8.6 ml) was added to a stirred solution of 3-methoxysalicylaldehyde (10 g), potassium carbonate (14.76 g) and potassium iodide (0.12 g) in DMF (120 ml) under an atmosphere of argon. The reaction was heated at 70° C. for 16 hours. Water (200 ml) was added causing the precipitation of a brown oil which crystallised on cooling. The solid was filtered, washed with water, dissolved in dichloromethane and dried (MgSO$_4$). The solvent was removed in vacuo to give an oil which crystallised on trituration with iso-hexane to give the product as an off white solid (12.85 g, 81%); NMR d (CD$_3$SOCD$_3$) 3.91 (s, 3H), 5.15 (s, 2H), 7.14–7.22 (m, 2H), 7.29–7.42 (m, 6H), 10.10 (t, 1H); M/z (+) 243 (MH$^+$).

PREPARATION 7

Methyl Azidoacetate

Methyl bromoacetate (62 ml) was added to a suspension of sodium azide (44 g) in DMF (500 ml) at ambient temperature and the reaction stirred for 16 hours. The reaction was poured into ice-water (1000 g) and extracted with ether. Combined organic extracts were washed with water and brine, dried (MgSO$_4$) and concentrated to give the product as a colourless oil which was used without further purification (64.2 g, 82%); NMR d (CDCl$_3$) 3.80 (3H, s), 3.90 (2H, s).

PREPARATION 7a

Methyl Azidoacetate (Toluene Solution)

To a stirred solution of methyl bromoacetate (50 ml) and tetra-n-butylammonium hydrogen sulphate (3.4 g) in toluene (200 ml) at 20–25° C. was added dropwise a solution of sodium azide (36 g) and sodium carbonate (2.0 g) in water (150 ml) over 30 minutes. The mixture was stirred for a further hour, the organic layer separated and dried (MgSO$_4$) to give the product as a ca. 2M toluene solution (250 ml). The product was used without further characterisation.

PREPARATION 8

Methyl 4-Benzyloxy-5-methoxyindole-2-carboxylate

A solution of 2-benzyl-3-methoxybenzaldehyde (6 g) and methyl azido acetate (4.27 g) in methanol (45 ml) was added dropwise to a stirred solution of sodium methoxide (2.0 g) in methanol (60 ml) under argon at −40° C. The reaction was then stirred and allowed to warm to room temperature over 16 hours. The reaction was poured into ice water (100 ml) and extracted with diethyl ether. Combined organic extracts were washed with water, dried (MgSO$_4$) and carefully concentrated in vacuo. The residue was dissolved in xylene (15 ml) and added dropwise to a stirred flask of xylene (25 ml) at 160° C. The reaction was stirred for 1 hour then concentrated in vacuo and the residue purified by column chromatography using 35% diethyl ether: iso-hexane as eluent to give the product as a yellow solid (1.39 g, 42%); NMR d (CD$_3$SOCD$_3$) 3.79 (s, 3H), 3.82 (s, 3H), 5.18 (s, 2H), 7.10 (m, 2H), 7.30–7.40 (m, 6H), 11.78 (brs, 1H); M/z (+) 312 (MH$^+$).

PREPARATION 9

Methyl 2-(2-Benzyloxyphenyl)-1-azidoacrylate

To a commercial solution of 25% w/w sodium methoxide in methanol (500 ml) was added methanol (1 litre) and the mixture cooled to −20° C. with stirring. A solution of 2-benzyloxybenzaldehyde (125 g) and methyl azidoacetate (253 g) in toluene (1 litre) was added dropwise such that the reaction temperature did not exceed 0° C. The mixture was stirred for a further 3 hours at 0° C. and the pale yellow crystals filtered off and washed successively with cold methanol (500 ml) and 1N aqueous acetic acid (500 ml) to give the product (150 g, 82%); NMR d (CDCl$_3$) 3.88 (s, 3H), 5.15 (s, 2H), 6.92 (d, 1H), 7.00 (dd, 1H), 7.3–7.4 (m, 6H), 7.50 (s, 1H), 8.20 (dd, 1H).

PREPARATION 10

Methyl 4-Benzyloxyindole-2-carboxylate

A solution of methyl 2-(2-benzyloxyphenyl)-1-azidoacrylate (50 g) in o-xylene (500 ml) was added dropwise to refluxing o-xylene (200 ml) with stirring, nitrogen was evolved during 30 minutes. The pale yellow solution was allowed to cool and the resulting crystals were filtered and washed with toluene (200 ml) and then hexane (200 ml)

to give the product as white needles (39 g, 86%). NMR d (CD$_3$SOCD$_3$) 3.83 (s, 3H), 5.22 (s, 2H), 6.61 (d, 1H), 7.03 (d, 1H), 7.1–7.2 (m, 2H), 7.3–7.5 (m, 5H), 11.9 (brs, 1H).

PREPARATION 11

Methyl 4-Hydroxy-5-methoxyindole-2-carboxylate

5% Palladium on carbon (0.3 g) and methyl 4-benzyloxy-5-methoxyindole-2-carboxylate (2.0 g) in ethyl acetate (30 ml) were vigorously stirred under an atmosphere of hydrogen for 16 hours. The reaction was filtered through celite and the concentrated in vacuo to give the product as a cream solid (1.29 g, 91%); NMR d (CD$_3$SOCD$_3$) 3.74 (s, 3H), 3.82 (s, 3H), 6.80 (d, 1H), 7.00 (d, 1H), 7.16 (s, 1H), 9.10 (s, 1H), 11.58 (brs, 1H); M/z (+) 222 (MH$^+$).

PREPARATION 12

Methyl 4-Acetoxyindole-2-carboxylate

A solution of methyl 4-benzyloxyindole-2-carboxylate (48 g) in ethyl acetate (1 litre) at 50–60° C. was hydrogenated over 5%Pd-C catalyst (4.0 g) at 1 atmosphere pressure for 6 hours, until 3.7 litres of hydrogen was absorbed. The catalyst was filtered off and washed with warm ethyl acetate (100 ml). To the combined filtrates was added acetic anhydride (40 ml) and 4-dimethylaminopyridine (1.0 g), and the solution was stirred for 1 hour at 25° C. Ethanol (15 ml) was added and the solution reduced to halt volume by evaporation in vacuo, then hexane (1 litre) was added to cause crystallisation of the product as white needles (37 g, 93%). NMR d (CD$_3$SOCD$_3$) 2.34 (s, 3H), 3.85 (s, 3H), 6.80 (d, 1H), 7.06 (s, 1H), 7.23 (t, 1H), 7.29–7.35 (m, 1H), 12.1 (bs, 1H); M/z (−) 232 (M-H$^+$).

PREPARATION 13

Methyl 4Hydroxyindole-2-carboxylate

Boron tribromide (73.1 ml, 1.0 M solution in DCM) was added dropwise to a solution of methyl 4-methoxyindole-2-carboxylate (5 g) in DCM (200 ml) cooled to −78° C. under argon. The reaction was allowed to warm to room temperature then partitioned between dichloromethane and saturated aqueous sodium hydrogen carbonate solution. Combined organic extracts were dried (MgSO$_4$) and concentrated in vacuo and the residue purified by column chromatography using iso-hexane-50% ethyl acetate as eluent to give the end product as a yellow solid (2.98 g, 64%); NMR d (CD$_3$SOCD$_3$) 3.82 (s, 3H), 6.36 (d, 1H), 6.85 (d, 1H), 7.02 (t, 1H), 7.17 (d, 1H), 9.66 (s, 1H), 11.72 (bs, 1H); M/z (+) 192 (MH$^+$).

PREPARATION 14

Methyl 4-Acetoxy-5-methoxyindole-2-carboxylate

A stirred solution of methyl 4-hydroxy-5-methoxyindole-2-carboxylate (0.51 g) and DMAP (10 mg) in acetic anhydride (5 ml) was heated at 80° C. for 4 hours. The reaction was concentrated in vacuo and the residue dissolved in dichloromethane and washed with hydrochloric acid (2.0 M), saturated aqueous sodium hydrogen carbonate solution, water, aqueous saturated sodium chloride solution and dried (MgSO$_4$). The solution was concentrated in vacuo and the residue was purified by column chromatography using 50% diethyl ether:iso-hexane as eluent to give the product as a white solid (0.58 g, 75%), NMR d CD$_3$SOCD$_3$) 2.34 (s, 3H), 3.75 (s, 3H), 3.85 (s, 3H), 6.99 (d, 1H), 7.19 (d, 1H), 7.29 (d, 1H), 11.93 (brs, 1H); M/z (+) 264 (MH$^+$).

PREPARATION 15

The procedure describe in the Preparation 14 above was repeated using the appropriate hydroxyindole. Thus was obtained the compound described below.

Methyl 4-Acetoxyindole-2-carboxylate

72% yield; NMR d (CD$_3$SOCD$_3$) 2.34 (s, 3H), 3.85 (s, 3H), 6.80 (d, 1H), 7.06 (s, 1H), 7.23 (t, 1H), 7.29–7.35 (m, 1H), 12.1 (bs, 1H); M/z (−) 232 (M-H$^+$).

PREPARATION 16

Methyl 4-Acetoxy-N-(3,4-dichlorobenzyl)-5-methoxyindole-2-carboxylate 3,4-Dichlorobenzyl bromide (1.02 g) was added to a stirred solution of methyl 4-acetoxy-5-methoxyindole-2-carboxylate (0.8 g) and potassium carbonate (0.97 g) in acetonitrile (30 ml) under an atmosphere of argon. The reaction was heated at 80° C. for 16 hours, then concentrated in vacuo and the residue partitioned between ethyl acetate and water.

Combined organic extracts were washed with water, saturated aqueous sodium chloride solution and dried (MgSO$_4$). The solvent was removed in vacuo to give the product as a cream solid (1.05 g. 82%); NMR d CD$_3$SOCD$_3$) 2.36 (s, 3H), 3.78 (s, 3H), 3.80 (s, 3H), 5.80 (s, 2H), 6.92 (dd, 1H), 7.21 (s, 1H), 7.27 (d, 1H), 7.36 (d, 1H), 7.48 (d, 1H), 7.52 (d, 1H).

PREPARATION 17

The procedure described in Preparation 16 above were repeated using the appropriate indole and benzyl halide. Thus were obtained the compounds described below.

Methyl 4-Acetoxy-N-(3,4-dichlorobenzyl)indole-2-carboxylate

81% yield; NMR d (CD$_3$SOCD$_3$) 2.4 (s, 3H), 3.8 (s, 3H), 5.85 (s, 2H), 6.9 (m, 2H), 7.3 (m, 3H), 7.5 (m, 2H); M/z (+) 392.2 (MH$^+$).

Methyl 4-Acetoxy-N-(3,4-difluorobenzyl)indole-2-carboxylate

66% yield; NMR d (CD$_3$SOCD$_3$) 2.49 (s, 3H), 3.96 (s, 3H), 5.93 (s, 2H), 6.93–7.00 (m, 1H), 7.03 (d, 1H), 7.23–7.33 (m, 1H), 7.37–7.49 (m, 3H) 7.60 (d, 1H); M/z (+) 360 (MH$^+$).

Methyl 4-Acetoxy-N-benzylindole-2-carboxylate

78% yield; NMR d (CD$_3$SOCD$_3$) 2.38 (s, 3H), 3.81 (s, 3H), 5.85 (s, 2H), 6.89 (d, 1H), 7.05 (d, 2H), 7.17–7.34 (m, 5H), 7.48 (d, 1H).

Methyl 4-Acetoxy-N-(3-chlorobenzyl)indole-2-carboxylate

88% yield; NMR d (CD$_3$SOCD$_3$) 2.28 (s, 3H), 3.74 (s, 3H), 5.77 (s, 2H), 6.80–6.90 (m, 2H), 7.07 (s, 1H), 7.16–7.27 (m, 4H), 7.38 (d, 1H); M/z (+) 358 (MH$^+$).

Methyl 4-Acetoxy-N-(4-chlorobenzyl)indole-2-carboxylate

27% yield; NMR d (CD$_3$SOCD$_3$) 2.37 (s, 3H), 3.81 (s, 3H), 5.82 (s, 2H), 6.90 (d, 1H), 7.08 (d, 2H), 7.31 (dd, 1H), 7.49 (d, 1H); M/z (+) 358 (MH$^+$).

PREPARATION 18

Methyl N-(3,4-Dichlorobenzyl)-4-hydroxy-5-methoxyindole-2-carboxylate

Sodium methoxide (0.27 g) was added to a stirred solution of methyl 4-acetoxy-N-(3,4-dichlorobenzyl)-5-methoxyindole-2-carboxylate (1.05 g) in methanol (15 ml) under an atmosphere of argon. The reaction was stirred at room temperature for 2 hours, then concentrated in vacuo and the residue partitioned between ethyl acetate and water. Combined organic extracts were washed with water, saturated aqueous sodium chloride solution and dried ($MgSO_4$). The solvent was removed in vacuo and the residue purified by column chromatography using 45% diethyl ether: isohexane as eluent to give product as a white solid (0.83 g, 94%); NMR d ($CD_3SOCD_3$) 3.75 (s, 3H), 3.80 (s, 3H), 5.72 (s, 2H), 6.87–6.94 (m, 2H), 7.09 (d, 1H), 7.30 (s, 1H), 7.40 (s, 1H), 7.50 (d, 1H), 9.38 (s, 1H); M/z (+) 380 ($MH^+$).

PREPARATION 19

The procedure described in Preparation 18 above was repeated using the appropriate acetoxyindole. Thus was obtained the compound described below.

Methyl N-(3,4-Dichlorobenzyl)-4-hydroxyindole-2-carboxylate

97% yield; NMR d ($CD_3SOCD_3$) 3.8 (s, 3H), 5.65 (s, 2H), 6.5 (d, 1H), 6.9 (m, 2H), 7.1 (t, 1H), 7.3 (m, 1H), 7.45 (s, 1H), 7.5 (d, 1H), 9.9 (s, 1H); M/z (+) 350 ($MH^+$).

Methyl N-(3,4-Difluorobenzyl)-4-hydroxyindole-2-carboxylate

77% yield; NMR d ($CD_3SOCD_3$) 3.80 (s, 3H), 5.84 (s, 2H), 6.45 (d, 1H), 6.75–6.81 (m, 1H), 6.95 (d, 1H), 7.05–7.16 (m, 2H), 7.24–7.35 (m, 1H), 7.41 (s, 1H), 9.90 (s, 1H); M/z (+) 318 ($MH^+$).

Methyl N-Benzyl-4-hydroxyindole-2-carboxylate

90% yield; NMR d ($CD_3SOCD_3$) 3.80 (s, 3H), 5.77 (s, 2H), 6.43 (d, 1H), 6.90–7.28 (m, 7H), 7.40 (s, 1H), 9.88 (s, 1H); M/z (+) 282 ($MH^+$).

Methyl N-(3-Chlorobenzyl)-4-hydroxyindole-2-carboxylate

94% yield; NMR d ($CD_3SOCD_3$) 3.80 (s, 3H), 5.78 (s, 2H), 6.46 (d, 1H), 6.90–6.97 (m, 2H), 7.04–7.14 (m, 2H), 7.21–7.31 (m, 2H), 7.42 (s, 1H), 9.90 (s, 1H); M/z (+) 3 16 ($MH^+$).

Methyl N-(4-Chlorobenzyl)-4-hydroxyindole-2-carboxylate

77% yield; NMR d ($CD_3SOCD_3$) 3.80 (s, 3H), 5.75 (s, 2H), 6.45 (d, 1H), 6.94 (d, 1H), 7.00 (d, 2H), 7.10 (t, 1H), 7.30 (d, 2H), 7.40 (s, 1H), 9.89 (s, 1H); M/z (+) 316 ($MH^+$).

EXAMPLE 1

Ethyl N-(3,4-Dichlorobenzyl)-4-(3-hydroxypropylthio)indole-2-carboxylate (Ethyl Ester of Compound 19)

Sodium hydride (20 mg) was added to a stirred solution of ethyl N-(3,4-dichlorobenzyl)-4-mercaptoindole-2-carboxylate (170 mg) in DMF (7.5 ml). After 1 hour, 3-hydroxyprop-1-yl bromide (89 mg) was added and stirring continued for 16 hours. The reaction mixture was partitioned between water and ethyl acetate and combined organic extracts were dried ($MgSO_4$), concentrated in vacuo and the residue purified by column chromatography using dichloromethane as eluent to give the product as a yellow gum (30 mg, 14%); M/z (+) 480.1 ($MH^+$).

EXAMPLE 2

Ethyl N-(3,4-Dichlorobenzyl)-4-(3-hydroxypropylsulphonyl)indole-2-carboxylate (Ethyl Ester of Compound 20)

Ethyl N-(3,4-dichlorobenzyl)-4-(3-hydroxypropylthio)indole-2-carboxylate (30 mg) was suspended in acetic acid (1 ml) and stirred in the presence of hydrogen peroxide (30%, 0.25 ml) for 16 hours. The reaction mixture was diluted with water (20 ml) and extracted with ethyl acetate. Combined organic extracts were dried ($MgSO_4$) and concentrated in vacuo to give the desired product as a colorless gum (30 mg, 93%); M/z (+) 512.4 ($MH^+$).

EXAMPLE 3

Methyl N-Benzyl-4-(2-hydroxyethoxy)indole-2-carboxylate (Methyl Ester of Compound 1)

Potassium carbonate (0.2 g) was added to a stirred solution of methyl N-benzyl-4-hydroxyindole-2-carboxylate (0.2 g) and 2-Bromoethanol (98 mg) in DMF (15 ml). The reaction was then stirred for 16 hours at 80° C. under an atmosphere of argon. The reaction mixture was concentrated in vacuo and the residue partitioned between ethyl acetate and water. Combined organic extracts were washed with water, dried ($MgSO_4$), concentrated in vacuo and the residue purified by column chromatography using 70% ethyl acetate: isohexane as eluent to give the product as a colourless crystalline solid. (64 mg, 27%); NMR d ($CD_3SOCD_3$) 3.74–3.82 (m, 5H), 4.10 (m, 2H), 4.88 (m, 1H), 5.80 (s, 2H), 6.58 (m, 1H), 6.98 (d, 2H), 7.09 (m, 1H), 7.14–7.27 (m, 4H), 7.38 (m, 1H); M/z (+) 326 ($MH^+$).

EXAMPLE 4

The procedure described in Example 3 above was repeated using the appropriate hydroxyindole and alkyl halide. Thus were obtained the compounds described below.

Methyl N-Benzyl-4-(methoxyethoxy)indole-2-carboxylate (Methyl Ester of Compound 2)

55% yield; NMR d ($CD_3SOCD_3$) 3.35 (s, 3H), 3.74 (m, 2H), 3.79 (s, 3H), 4.21 (m, 2H), 5.80 (s, 2H), 6.60 (d, 1H), 6.99 (d, 2H), 7.12 (d, 1H), 7.15–7.28 (m, 4H), 7.30 (s, 1H); M/z (+) 340 ($MH^+$).

Methyl N-(3,4-Difluorobenzyl)-4-(methoxycarbonylmethoxy)indole-2-carboxylate (di-Methyl Ester of Compound 5)

NMR d ($CD_3SOCD_3$) 3.72 (s, 3H), 3.82 (s, 3H), 4.94 (s, 2H), 5.80 (s, 2H), 6.54 (d, 1H), 6.79 (m, 1H), 7.10–7.36 (m, 5H); M/z (+) 390 ($MH^+$).

Methyl N-(3-Chlorobenzyl)-4-(methoxycarbonylmethoxy)indole-2-carboxylate (di-Methyl Ester of Compound 6)

93% yield; NMR d ($CD_3SOCD_3$) 3.72 (s, 3H) 3.82 (s, 3H), 4.93 (s, 2H), 5.81 (s, 2H), 6.54 (d, 1H), 6.93 (m, 1H), 7.08 (s, 1H), 7.14–7.37 (m, 6H); M/z (+) 388 ($MH^+$).

Methyl N-Benzyl-4-(1-methoxycarbonyl-1-phenylmethoxy)indole-2-carboxylate (di-Methyl Ester of Compound 7)

42% yield; NMR d (CD$_3$SOCD$_3$) 3.66 (s, 3H), 3.80 (s, 3H), 5.81 (s, 2H), 6.13 (s, 1H), 6.56 (dd, 1H), 7.00 (d, 2H), 7.14–7.29 (m, 5H), 7.37–7.50 (m, 4H), 7.62 (d 2H); M/z (+) 430 (MH$^+$).

Methyl N-(4-Chlorobenzyl)-4-(methoxycarbonylmethoxy)indole-2-carboxylate (di-Methyl Ester of Compound 8)

93% yield; NMR d (CD$_3$SOCD$_3$) 3.71 (s, 3H), 3.80 (s, 3H), 4.92 (s, 2H), 5.80 (s, 2H), 6.52 (d, 1H), 7.01 (d, 2H), 7.12–7.23 (m, 2H), 7.31 (m, 3H); M/z (+) 388 (MH$^+$).

Methyl N-(3,4-Dichlorobenzyl)-4-(2-(methoxycarbonyl)ethoxy)indole-2-carboxylate (Methyl di-Ester of Compound 12)

89% yield; NMR d (CD$_3$SOCD$_3$) 1.59 (d, 3H), 3.68 (s, 3H), 3.80 (s, 3H), 5.08 (q, 1H), 5.79 (s, 2H), 6.47 (d, 1H), 6.89 (dd, 1H), 7.14–7.24 (m, 2H), 7.33–7.36 (m, 2H), 7.51 (d, 1H); M/z (+) 436 (MH$^+$).

Methyl N-(3,4-Dichlorobenzyl)-4-[2-(2-methoxy-4-methoxycarbonylphenyl)ethoxy]-indole-2-carhoxylate (di-Methyl Ester of Compound 13)

64% yield; NMR d (CD$_3$SOCD$_3$) 3.80 (s, 3H), 3.86 (s, 3H)), 3.91 (s, 3H), 5.26 (s, 2H), 5.80 (s, 2H), 6.68 (d, 1H), 6.88 (dd, 1H), 7.16 (d, 1H), 7.25 (t, 1H), 7.33 (d, 1H), 7.40 (s, 1H), 7.50 (d, 1H), 7.54 (d, 1H), 7.59–7.69 (m, 2H); M/z (+) 528 (MH$^+$).

Methyl N-(3,4-Dichlorobenzyl)-4-(2-hydroxyethoxy)indole-2-carboxylate (Methyl Ester of Compound 14)

63% yield; NMR d (CD$_3$SOCD$_3$) 3.75–3.81 (m, 5H), 4.10 (t, 2H), 4.88 (t, 1H), 5.80 (s, 2H), 6.60 (d, 1H), 6.88 (dd, 1H), 7.12 (d, 1H), 7.22 (t, 1H), 7.28 (d, 1H), 7.40 (s, 1H), 7.50 (d, 1H); M/z (+) 394 (MH$^+$).

Methyl N-(3,4-Dichlorobenzyl)-4-(3-hydroxypropoxy)indole-2-carboxylate (Methyl Ester of Compound 15)

75% yield; NMR d (CD$_3$SOCD$_3$) 1.92 (s, 2H), 3.60 (dd, 2H), 4.17 (t, 2H), 4.53 (t, 1H), 5.79 (s, 2H), 6.61 (d, 1H), 6.87 (dd, 1H), 7.12 (d, 1H), 7.24 (t, 1H), 7.29–7.34 (m, 2H), 7.51 (d, 1H); M/z (+) 408 (MH$^+$).

Methyl N-(3,4-Dichlorobenzyl)-4-(dimethylaminoethyloxy)indole-2-carboxylate (Methyl Ester of Compound 18)

NMR d (CD$_3$SOCD$_3$) 2.26 (s, 6H), 2.71 (t, 2H), 3.80 (s, 3H), 4.18 (t, 2H), 5.79 (s, 2H), 6.61 (d, 1H), 6.87 (dd, 1H), 7.12 (d, 1H), 7.21 (d, 1H), 7.26–7.31 (m, 2H), 7.50 (d, 1H); M/z (+) 421 (MH$^+$).

Methyl N-(3,4-Dichlorobenzyl)-5-methoxy-4-(methoxycarbonylmethoxy)indole-2-carboxylate (di-Methyl Ester of Compound 9)

87% yield; NMR d (CD$_3$SOCD$_3$) 3.67 (s, 3H), 3.79 (s, 3H), 3.82 (s, 3H), 4.83 (s, 2H), 5.79 (s, 2H), 6.90 (m, 1H), 7.16–7.30 (m, 2H), 7.36 (s, 2H), 7.52 (d, 1H); M/z (+) 452 (MH$^+$).

Methyl N-(3,4-Dichlorobenzyl)-5-methoxy-4-(3-morpholinopropoxy)indole-2-carboxylate (Methyl Ester of Compound 10)

84% yield; NMR d (CD$_3$SOCD$_3$) 1.86 (m, 2H), 2.24–2.44 (m, 6H), 3.50–3.60 (m, 4H), 3.78 (s, 3H), 3.80 (s, 3H), 4.16 (t, 2H), 5.78 (s, 2H), 6.90 (d, 1H), 7.16 (d, 1H), 7.23 (d, 1H), 7.34 (m, 2H), 7.51 (d, 1H); M/z (+) 507 (MH$^+$).

Methyl N-(3,4-Dichlorobenzyl)-5-methoxy-4-carbamoylmethoxyindole-2-carboxylate (Methyl Ester of Compound 11)

74% yield; NMR d (CD$_3$SOCD$_3$) 3.80 (s, 3H), 3.81 (s, 3H), 4.52 (s, 2H), 5.77 (s, 2H), 6.89 (dd, 1H), 7.18–7.61 (m, 7H); M/z (+) 437 (MH$^+$).

Methyl N-(3,4-Dichlorobenzyl)-4-(2,3-epoxypropyloxy)indole-2-carboxylate (Precursor to 16, 17, 22, 23, 24, 25, 26, 27 and 28)

60% yield; NMR d (CD$_3$SOCD$_3$) 2.78 (m, 1H), 2.87 (m, 1H), 3.40 (m, 1H), 4.00 (dd, 1H), 4.46 (dd, 1H), 5.80 (s, 1H), 6.65 (d, 1H), 6.88 (dd, 1H), 7.16 (d, 1H), 7.24 (t, 1H), 7.31 (d, 1H), 7.36 (s, 1H), 7.50 (d, 1H); M/z (+) 406 (MH$^+$).

EXAMPLE 5

N-Benzyl-4-(3-morpholinopropoxy)indole-2-carboxylic Acid (Compound 3)

N-3-chloropropylmorpholine (128 mg) was added to a stirred solution of methyl N-(3,4-dichlorobenzyl)-4-hydroxyindole-2-carboxylate (0.2 g) and potassium carbonate (0.2 g) in DMF (3 ml). The reaction was then stirred for 48 hours at 80° C. under an atmosphere of argon. Water (4 ml) was added and the product was extracted with ethyl acetate. Combined organic extracts were washed with water and dried (MgSO$_4$), concentrated in vacuo and the residue purified by column chromatography using 10% methanol dichloromethane as eluent to give the product as a light brown gum. The product was used without further purification.

Aqueous sodium hydroxide solution (2.0 M, 4 ml) was added to a stirred solution of the product in methanol (2 ml) and THF (4 ml). The reaction was stirred for 16 hours at room temperature. The solvent was removed in vacuo and the residue dissolved in water. Aqueous citric acid (1.0 M) was added to the solution causing the precipitation of the product as a white solid. The solid was filtered and dried in vacuo (220 mg, 80%, 2 steps); NMR d (CD$_3$SOCD$_3$) 1.94 (m, 2H), 2.37 (m, 4H), 3.55 (m, 6H), 4.12 (t, 2H), 5.87 (s, 2H), 6.55 (d, 2H), 6.96–7.28 (m, 8H); M/z (−) 393 (M−H$^+$).

EXAMPLE 6

The procedure described in Example 5 above was repeated using the appropriate alkyl halide. Thus was obtained the compound described below.

N-Benzyl-4-(3-(4-methylpiperazin-1-yl)propoxy)indole-2-carboxylic Acid (Compound 4)

72% yield (2 steps); NMR d (CD$_3$OD) 2.34 (m, 2H), 2.92 (s, 3H), 3.50 (t, 2H), 3.62–3.84 (d, 8H), 4.41 (t, 2H), 5.80 (s, 2H), 6.50 (d, 1H) 6.94–7.04 (m, 3H), 7.09–7.26 (m, 4H), 7.57 (s, 1H); M/z (−) 406 (M−H$^+$).

EXAMPLE 7

N-(3,4-Dichlorobenzyl)-4-(2-hydroxy-3-dimethylaminopropoxy)indole-2-carboxylic Acid (Compound 16)

Dimethylamine in methanol (2.0 M, 2.14 ml) was added to a stirred solution of methyl N-(3,4-dichlorobenzyl)-4-(2, 3-epoxypropyloxy)indole-2-carboxylate (87 mg) in DMF (5 ml) under an atmosphere of argon. The reaction was heated at 80° C. for 16 hours. The reaction was concentrated in vacuo and the residue partitioned between ethyl acetate and water. Combined organic extracts were washed with saturated aqueous sodium chloride solution, dried (MgSO$_4$) and concentrated in vacuo. The residue was dissolved in THF (3 ml) and methanol (1.5 ml) and NaOH (2M, 3 ml) added and the reaction stirred for 16 hours. The reaction was then concentrated in vacuo and the residue dissolved in water. The solution was acidified by dropwise addition of acetic acid, resulting in the precipitation of a white solid which was filtered, washed with water and dried in vacuo to give the desired end product as a white solid (50 mg, 54%, 2 steps); NMR d (CD$_3$SOCD3) 2.85 (s, 6H), 3.22–3.40 (m, 2H), 4.01–4.14 (m, 1H), 5.81 (s, 2H), 6.01 (d, 1H), 6.60 (d, 1H), 6.88 (dd, 1H), 7.13 (d, 1H), 7.21 (t, 1H), 7.28 (d, 1H), 7.44 (s, 1H), 7.53 (d, 1H); M/z (−) 435 (M−H$^+$).

EXAMPLE 8

The procedure described in Example 7 above was repeated using the appropriate amines. Thus were obtained the compounds described below.

N-(3,4-Dichlorobenzyl)-4-(2-hydroxy-3-morpholinodropoxy)indole-2-carboxylic Acid (Compound 17)

36% yield (2 steps); NMR d (CD$_3$SOCD$_3$) 2.83–3.41 (M, 6H), 3.65–3.84 (M, 4H), 4.07 (d, 2H), 4.31 (M, 1H), 5.80 (s, 2H), 6.60 (d, 1H), 6.89 (dd, 1H), 7.12 (d, 1H), 7.21 (t, 1H), 7.29 (d, 1H), 7.41 (s, 1H), 7.52 (d, 1H); M/z (+) 479 (MH$^+$).
Compound 23
13% yield (2 steps); M/z (−) 505.4 (M−H$^+$).
Compound 24
8% yield (2 steps); M/z (−) 520.3 (M−H$^+$).
Compound 25
30% yield (2 steps); M/z (−) 491.3 (M−H$^+$).
Compound 26
75% yield (2 steps); M/z (−) 523.4 (M−H$^+$).
Compound 27
66% yield (2 steps); M/z (−) 505.4 (M−H$^+$).
Compound 28
17% yield (2 steps); M/z (−) 465.2 (M−H$^+$).

EXAMPLE 9

N-(3,4-Dichlorobenzyl)-4-(2,3-dihydroxypropoxy) indole-2-carboxylic Acid (Compound 21)

Ethyl N-(3,4-dichlorobenzyl)-4-(2,3-dihydroxypropoxy) indole-2-carboxylate (85 mg) was dissolved in THF (3 ml) and methanol (1 ml) and sodium hydroxide (2M, 3.0 ml) was added and the reaction stirred for 16 hours. The reaction was then concentrated in vacuo and the residue dissolved in water. The solution was acidified by dropwise addition of acetic acid, resulting in the precipitation of a white solid which was filtered, washed with water and dried in vacuo to give the desired end product (70 mg, 81%); NMR d (CD$_3$SOCD$_3$) 3.40–3.53 (m, 3H), 3.98–4.10 (m, 2H), 5.80 (s, 2H), 6.59 (d, 1H), 6.88 (d, 1H), 7.09 (d, 1H), 7.20 (t, 1H), 7.30 (d, 1H), 7.36 (s, 1H), 7.51 (d, 1H); M/z (−) 408 (M−H$^+$).

EXAMPLE 10

Methyl N-(3,4-Dichlorobenzyl)-4-(2-(4-(2-hydroxyethyl)piperazin-1-yl)ethoxy)indole-2-carboxylate (Methyl Ester of Compound 22)

Triphenylphosphine (0.55 g) was added in small portions over 2 hours to a stirred solution of carbon tetrabromide (0.47 g) and methyl N-(3,4-diclilorobenzyl)-4-(hydroxyethyloxy)indole-2-carboxylate (0.28 g) in dichloromethane (10 ml). The reaction was stirred for 3 hours at room temperature, concentrated in vacuo and the residue purified by column chromatography using dichloromethane as eluent to give methyl N-(3,4-dichlorobenzyl)-4-(bromoethyloxy)indole-2-carboxylate as a white solid (0.29 g, 90%); NMR d (CD$_3$SOCD$_3$) 3.80 (s, 3H), 3.89 (t, 2H), 4.46 (t, 2H), 5.80 (s, 2H), 6.62 (d, 1H), 6.88 (dd, 1H), 7.17 (d, 1H), 7.25 (t, 1H), 7.30–7.36 (m, 2H), 7.52 (d, 1H), M/z (+) 456, 458 (MH$^+$).

1-(2-Hydroxyethyl)piperazine (175 mg) was added to a stirred solution of methyl N-(3,4-dichlorobenzyl)-4-(bromoethyloxy)indole-2-carboxylate (278 mg) and potassium iodide (10 mg) in acetonitrile (15 ml). The reaction was heated at 80° C. for 16 hours. The reaction was concentrated in vacuo and the residue dissolved in ethyl acetate, washed with water, saturated aqueous sodium chloride solution and dried (MgSO$_4$). The solvent was removed in vacuo to give the product as a colourless oil (215 mg, 70%); NMR d (CD$_3$SOCD$_3$) 2.31–2.57 (m, 10H), 2.78 (t, 2H), 3.47 (dd, 2H), 3.80 (s, 3H), 4.20 (t, 2H), 4.30 (t, 1H), 5.79 (s, 2H), 6.61 (d, 1H), 6.88 (dd, 1H), 7.13 (d, 1H), 7.22 (t, 1H), 7.29–7.32 (m, 2H), 7.51 (d, 1H); M/z (+) 506 (MH$^+$).

EXAMPLE 11

N-(3,4-Dichlorobenzyl)-4-(3-hydroxypropoxy) indole-2-carboxylic Acid (Compound 15)

Methyl N-(3,4-Dichlorobenzyl)-4-(3-hydroxypropyloxy) indole-2-carboxylate (6.9 g) was dissolved in THF (140 ml) and methanol (140 ml) and sodium hydroxide (3M, 110 ml) was added and the reaction stirred for 16 hours. The reaction was then concentrated in vacuo and the residue dissolved in water. The solution was acidified by dropwise addition of acetic acid, resulting in the precipitation of a white solid which was filtered, washed with water and dried in vacuo to give the desired end product (5.58 g. 84%); NMR d (CD$_3$SOCD$_3$) 1.92 (m, 2H), 3.60 (dd, 2H), 4.13 (dd, 2H), 5.89 (s, 2H), 6.52 (s, 1H), 6.94–7.11 (m, 4H), 7.32 (d, 1H), 7.47 (d, 1H); M/z (−) 392 (M−H$^+$).

EXAMPLE 12

Using procedures similar to that described in Example 11 above but with the appropriate starting materials, the following compounds were prepared.

N-(3,4-Dichlorobenzyl)-4-(3-hydroxypropylthio) indole-2-carboxylic Acid (Compound 19)

70% yield; M/z (−) 408.3 (M−H$^+$).

N-(3,4-Dichlorobenzyl)-4-(3-hydroxypropylsulphonyl)indole-2-carboxylic Acid (Compound 20)

41% yield; M/z (−) 440.3 (M−H$^+$).

N-Benzyl-4-(2-hydroxyethyloxy)indole-2-carboxylic Acid (Compound 1)

82% yield; NMR d (CD$_3$SOCD$_3$) 3.78 (d, 2H), 4.08 (t, 2H), 4.87 (m, 1H), 5.82 (s, 2H), 6.56 (d, 1H), 6.98 (d, 2H), 7.06 (d, 1H), 7.14–7.27 (m, 4H), 7.32 (s, 1H); M/z (−) 310 (M−H$^+$).

N-Benzyl-4-(2-methoxyethoxy)indole-2-carboxylic Acid (Compound 2)

91% yield; NMR d (CD$_3$SOCD$_3$) 3.35 (s, 3H), 3.74 (m, 2H), 4.20 (m, 2H), 5.81 (s, 2H), 6.57 (d, 1H), 6.99 (d, 2H), 7.08 (d, 1H), 7.14–7.27 (m, 5H), 12.84 (brs, 1H); M/z (−) 324 (M−H$^+$).

N-(3,4-Difluorobenzyl)-4-(carboxymethoxy)indole-2-carboxylic Acid (Compound 5)

86% yield (2 steps); NMR d (CD$_3$SOCD$_3$) 4.79 (s, 2H), 5.80 (s, 2H), 6.48 (d, 1H), 6.78 (m, 1H), 7.08–7.36 (m, 5H), 12.98 (brs, 1H); M/z (−) 360 (M−H$^+$).

N-(3-Chlorobenzyl)-4-(carboxymethoxy)indole-2-carboxylic Acid (Compound 6)

89% yield; NMR d (CD$_3$SOCD$_3$) 4.79 (s, 2H), 5.81 (s, 2H), 6.45 (d, 1H), 6.91 (d, 1H), 7.05–7.31 (m, 6H); M/z (−) 358 (M−H$^+$).

N-Benzyl-4-(1-carboxy-1-phenylmethoxy)indole-2-carboxylic Acid (Compound 7)

80% yield; NMR d (CD$_3$SOCD$_3$) 5.81 (s, 2H), 5.94 (s, 1H), 6.52 (d, 1H), 7.00 (d, 2H), 7.09–7.29 (m, 5H), 7.33–7.48 (m, 4H), 7.62 (d, 2H); M/z (−) 400 (M−H$^+$).

N-(4-Chlorobenzyl)-4-(carboxymethoxy)indole-2-carboxylic Acid (Compound 8)

66% yield; NMR d (CD$_3$SOCD$_3$) 4.79 (s, 2H), 5.81 (s, 2H), 6.48 (d, 1H), 7.00 (d, 2H), 7.06–7.20 (m, 2H), 7.26–7.34 (m, 3H), 12.95 (brs, 1H); M/z (−) 358 (M−H$^+$).

N-(3,4-Dichlorobenzyl)-4-(1-carboxyethoxy)indole-2-carboxylic Acid (Compound 12)

90% yield; NMR d (CD$_3$SOCD$_3$) 1.58 (d, 3H), 4.91 (q, 1H), 5.80 (s, 2H), 6.42 (d, 1H), 6.88 (dd, 1H), 7.08–7.21 (m, 2H), 7.29 (s, 1H), 7.31 (d, 1H), 7.50 (d, 1H), M/z (−) 406 (M−H$^+$).

N-(3,4-Dichlorobenzyl)-4-(2-(4-carboxy-2-methoxyphenyl)ethoxy))indole-2-carboxylic Acid (Compound 13)

81% yield; NMR d (CD$_3$SOCD$_3$) 3.91 (s, 3H), 5.26 (s, 2H), 5.81 (s, 2H); 6.66 (d, 1H), 6.90 (dd, 1H), 7.10–7.25 (m, 2H), 7.32–7.36 (m, 2H), 7.48–7.56 (m, 2H), 7.59–7.65 (m, 2H), 12.97 (brs, 1H); M/z (−) 498 (M−H$^+$).

N-(3,4-Dichlorobenzyl)-4-(2-hydroxyethoxy)indole-2-carboxylic Acid (Compound 14)

83% yield; NMR d (CD$_3$SOCD$_3$) 3.77 (m, 2H), 4.08 (t, 2H), 4.89 (m, 1H), 5.80 (s, 2H), 6.58 (d, 1H), 6.89 (dd, 1H), 7.08 (d, 1H), 7.19 (t, 1H), 7.29 (d, 1H), 7.34 (s, 1H), 7.50 (d, 1H); M/z (−)378 (M−H$^+$).

N-(3,4-Dichlorobenzyl)-4-(dimethylaminoethyloxy)indole-2-carboxylic Acid (Compound 18)

13% yield (2 steps); NMR d (CD$_3$SOCD$_3$) 2.89 (s, 6H), 3.59 (t, 2H), 4.45 (t, 2H), 5.81 (s, 2H), 6.64 (d, 1H), 6.90 (dd, 1H), 7.18 (d, 1H), 7.22 (d, 1H), 7.28 (m, 1H), 7.48–7.54 (m, 2H); M/z (−) 405 (M−H$^+$).

N-(3,4-Dichlorobenzyl)-4-(2-(4-(2-hydroxyethyl)piperazin-1-yl)ethoxy)indole-2-carboxylic Acid (Compound 22)

90% yield; NMR d (CD$_3$SOCD$_3$) 2.40–2.67 (m, 10H), 2.81 (t, 2H), 3.49 (dd, 2H), 4.20 (t, 2H), 5.82 (s, 2H), 6.59 (d, 1H), 6.92 (dd, 1H), 7.06 (d, 1H), 7.11–7.19 (m, 2H), 7.30 (s, 1H), 7.50 (d, 1H); M/z (−) 490 (M−H$^+$).

N-(3,4-Dichlorobenzyl)-5-methoxy-4-(carboxymethoxy)indole-2-carboxylic Acid (Compound 9)

91% yield; NMR d (CD$_3$SOCD$_3$) 3.77 (s, 3H), 4.64 (s, 2H), 5.78 (s, 2H), 6.91 (dd, 1H), 7.13 (d, 1H), 7.20 (d, 1H), 7.30 (s, 1H), 7.35 (d, 1H), 7.51 (d, 1H); M/z (−) 424 (M−H$^+$).

N-(3,4-Dichlorobenzyl)-5-methoxy-4-(3-morpholinopropoxy)indole-2-carboxylic Acid (Compound 10)

94% yield; NMR d (CD$_3$SOCD$_3$) 2.17 (m, 2H), 3.10 (m, 2H), 3.34 (m, 4H), 3.72 (t, 2H), 3.80 (s, 3H), 3.97 (m, 2H), 4.20 (t, 2H), 5.79 (s, 2H), 6.93 (dd, 1H), 7.16 (d, 1H), 7.25 (d, 1H), 7.31 (s, 1H), 7.34 (d, 1H), 7.52 (d, 1H); M/z (+) 493 (MH$^+$).

EXAMPLE 13

N-(3,4-Dichlorobenzyl)-5-methoxy-4-(carbamoylmethoxy)indole-2-carboxylic Acid (Compound 11)

Lithium iodide (0.39 g) was added to stirred solution of methyl N-(3,4-dichlorobenzyl)-5-methoxy-4-carbamoylmethoxyindole-2-carboxylate (0.12 g) in pyridine (10 ml) under an atmosphere of argon. The reaction was then heated at 115° C. for 16 hours. The solvent was removed in vacuo and the residue was partitioned between ethyl acetate and hydrochloric acid (2.0 M, 10 ml). Combined organic extracts were washed with water and saturated aqueous sodium chloride solution, dried (MgSO$_4$) and concentrated in vacuo to give the product as a cream coloured solid (35 mg, 30%); NMR d (CD$_3$SOCD$_3$) 3.80 (s, 3H), 4.51 (s, 2H), 5.79 (s, 2H), 6.90 (dd, 1H), 7.18 (d, 1H), 7.25 (d, 1H), 7.34 (d, 1H), 7.39 (s, 1H), 7.42 (brs, 1H), 7.51 (d, 1H), 7.57 (brs, 1H), 13.05 (brs, 1H); M/z (−) 421 (M−H$^+$).

EXAMPLE 14

Biological Testing

The following biological test methods, data and Examples serve to illustrate the present invention.

Abbreviations:

| | |
|---|---|
| ATCC | American Type Culture Collection, Rockville, USA. |
| BCA | Bicinchroninic acid, (used, with copper sulphate, to assay protein) |
| BSA | Bovine Serum Albumin |
| DMEM | Dulbecco's modified Eagle's medium |
| EGTA | Ethylenebis(oxyethylenenitrilo)tetraacetic acid |
| FCS | Foetal calf serum |
| HEPES | (N-[2-Hydroxyethyl]piperazine-N'-[2-ethanesulphonic acid]) |
| HBSS | Hank's Balanced Salt Solution |
| hMCP-1 | Human Monocyte Chemoattractant Protein-1 |
| PBS | Phosphate buffered saline |

PCR Polymerase chain reaction

AMPLITAQ™, available from Perkin-Elmer Cetus, is used as the source of thermostable DNA polymerase.

Binding Buffer is 50 mM HEPES, 1 mM CaCl$_2$, 5 mM MgCl$_2$, 0.5% foetal calf serum, adjusted to pH 7.2 with 1 M NaOH.

Non-Essential Amino Acids (100×concentrate) is: L-Alanine, 890 mg/l; L-Asparagine, 1320 mg/l; L-Aspartic acid, 1330 mg/l; L-Glutamic acid, 1470 mg/l; Glycine, 750 mg/l; L-Proline, 1150 mg/l and; L-Serine, 1050 mg/l.

Hypoxanthine and Thymidine Supplement (50× concentrate) is: hypoxanthine, 680 mg/l and; thymidine, 194 mg/l.

Penicillin-Streptomycin is: Penicillin G (sodium salt); 5000 units/ml; Streptomycin sulphate, 5000 μg/ml.

Human monocytic cell line THP-1 cells are available from ATCC, accession number ATCC TIB-202.

Hank's Balanced Salt Solution (HBSS) was obtained from Gibco; see *Proc. Soc. Exp. Biol. Med.*, 1949, 71, 196.

Synthetic cell culture medium, RPMI 1640 was obtained from Gibco; it contains inorganic salts [Ca(NO$_3$)$_2$.4H$_2$O 100 mg/l; KCl 400 mg/l; MgSO$_4$.7H$_2$O 100 mg/l; NaCl 6000 mg/l; NaHCO$_3$ 2000 mg/l & Na$_2$HPO$_4$ (anhyd) 800 mg/l], D-Glucose 2000 mg/l, reduced glutathione 1 mg/l, amino acids and vitamins.

FURA-2/AM is 1-[2-(5-carboxyoxazol-2-yl)-6-aminoberzofuran-5-oxy]-2-(2'-amino-5'-methylphenoxy)-ethane-N,N,N',N'-tetraacetic acid pentaacetoxymethyl ester and was obtained from Molecular Probes, Eugene, Oreg., USA.

Blood Sedimentation Buffer contains 8.5 g/l NaCl and 10 g/l hydroxyethyl cellulose.

Lysis Buffer is 0.15M NH$_4$Cl$^-$, 10 mM KHCO$_3$, 1 mM EDTA

Whole Cell Binding Buffer is 50 mM HEPES, 1 mM CaCl$_2$, 5 mM MgCl$_2$, 0.5% BSA, 0.01% NaN$_3$, adjusted to pH 7.2 with 1M NaOH.

Wash buffer is 50 mM HEPES. 1 mM CaCl$_2$, 5 mM MgCl$_2$, 0.5% heat inactivated FCS, 0.5M NaCl adjusted to pH7.2 with 1M NaOH.

General molecular biology procedures can be followed from any of the methods described in "Molecular Cloning—A Laboratory Manual" Second Edition, Sambrook, Fritsch and Maniatis (Cold Spring Harbor Laboratory, 1989).

i) Cloning and Expression of hMCP-1 Receptor

The MCP-1 receptor B (CCR2B) cDNA was cloned by PCR from THP-1 cell RNA using suitable oligonucleotide primers based on the published MCP-1 receptor sequences (Charo et al., 1994, *Proc. Natl. Acad. Sci. USA*, 91, 2752). The resulting PCR products were cloned into vector PCR-II™ (In Vitrogen, San Diego, Calif.). Error free CCR2B cDNA was subcloned as a Hind III-Not I fragment into the eukaryotic expression vector pCDNA3 (In Vitrogen) to generate pCDNA3/CC-CKR2A and pCDNA3/CCR2B respectively.

Linearised pCDNA3/CCR2B DNA was transfected into CHO-K1 cells by calcium phosphate precipitation (Wigler el al., 1979, *Cell*, 16, 777). Transfected cells were selected by the addition of Geneticin Sulphate (G418, Gibco BRL) at 1 mg/ml, 24 hours after the cells had been transfected. Preparation of RNA and Northern blotting were carried out as described previously (Needham et al., 1995, *Prot. Express. Purific.*, 6, 134). CHO-K1 clone 7 (CHO-CCR2B) was identified as the highest MCP-1 receptor B expresser.

ii) Preparation of Membrane Fragments

CHO-CCR2B cells were grown in DMEM supplemented with 10% foetal calf serum, 2 mM glutamine, 1×Non-Essential Amino Acids, 1×Hypoxanthine and Thymidine Supplement and Penicillin-Streptomycin (at 50 µg streptomycin/ml, Gibco BRL). Membrane fragments were prepared using cell lysis/differential centrifugation methods as described previously (Siciliano el al., 1990, *J. Biol. Chem.*, 265, 19658). Protein concentration was estimated by BCA protein assay (Pierce, Rockford, Ill.) according to the manufacturer's instructions.

iii) Assay $^{125}$I MCP-1 was prepared using Bolton and Hunter conjugation (Bolton et al. 1973, *Biochem. J.*, 133, 529; Amersham International plc]. Equilibrium binding assays were carried out using, the method of Ernst et al., 1994, *J. Immunol.*, 152, 3541. Briefly, varying amounts of $^{125}$I-labeled MCP-1 were added to 7 µg of purified CHO-CCR2B cell membranes in 100 µl of Binding Buffer. After 1 hour incubation at room temperature the binding reaction mixtures were filtered and washed 5 times through a plate washer (Brandel MLR-96T Cell Harvester) using ice cold Binding Buffer. Filter mats (Brandel GF/B) were pre-soaked for 60 minutes in 0.3% polyethylenimine prior to use. Following filtration individual filters were separated into 3.5 ml tubes (Sarstedt No. 55.484) and bound $^{125}$I-labeled MCP-1 was determined (LKB 1277 Gammamaster). Cold competition studies were performed as above using 100 pM $^{125}$I-labeled MCP-1 in the presence of varying concentrations of unlabelled MCP-1. Non-specific binding was determined by the inclusion of a 200-fold molar excess of unlabelled MCP-1 in the reaction.

Ligand binding studies with membrane fragments prepared from CHO-CCR2B cells showed that the CCR2B receptor was present at a concentration of 0.2 pmoles/mg of membrane protein and bound MCP-1 selectively and with high affinity (IC$_{50}$=110 pM, K$_d$=120 pM). Binding to these membranes was completely reversible and reached equilibrium after 45 minutes at room temperature, and there was a linear relationship between MCP-1 binding and CHO-CCR2B cell membrane concentration when using MCP-1 at concentrations between 100 pM and 500 pM.

Test compounds dissolved in DMSO (5 µl) were tested in competition with 100 pM labelled MCP-1 over a concentration range (0.01–50 µM) in duplicate using eight point dose-response curves and IC$_{50}$ concentrations were calculated.

Compounds tested of the present invention had IC$_{50}$ values of 50 µM or less in the hMCP-1 receptor binding assay described herein. For example, compound 5 in Table 1 had an IC$_{50}$ of 2.3 µM.

b) MCP-1 Mediated Calcium Flux in THP-1 Cells

The human monocytic cell line THP-1 was grown in a synthetic cell culture medium RPMI 1640 supplemented with 10% foetal calf serum, 6 mM glutamine and Penicillin-Streptomycin (at 50 µg streptomycin/ml, Gibco BRL). THP-1 cells were washed in HBSS (lacking Ca$^{2+}$ and Mg$^{2+}$)+1 mg/ml BSA and resuspended in the same buffer at a density of 3×10$^6$ cells/ml. The cells were then loaded with 1 mM FURA-2/AM for 30 min at 37° C., washed twice in HBSS, and resuspended at 1×10$^6$ cells/ml. THP-1 cell suspension (0.9 ml) was added to a 5 ml disposable cuvette containing a magnetic stirrer bar and 2.1 ml of prewarmed (37° C.) HBSS containing 1 mg/ml BSA. 1 mM MgCl$_2$ and 2 mM CaCl$_2$. The cuvette was placed in a fluorescence spectrophotometer (Perkin Elmer, Norwalk, Conn.) and pre-incubated for 4 min at 37° C. with stirring. Fluorescence was recorded over 70 sec and cells were stimulated by addition of hMCP-1 to the cuvette after 10 sec. [Ca$^{2+}$]i was measured by excitation at 340 nm and 380 nm alternately and subsequent measurement of the intensity of the fluorescence emission at 510 nm. The ratio of the intensities of the emitted fluorescent light following excitation at 340 nm and 380 nm, (R), was calculated and displayed to give and estimate of cytoplasmic [Ca$^{2+}$] according to the equation:

$$[Ca^{2+}]i = K_d \frac{(R - Rmin)}{(Rmax - R)}(Sf2/Sb2)$$

where the K$_d$ for FURA-2 Ca$^{2+}$ complex at 37° C. was taken to be 224 nm. R$_{max}$ is the maximal fluorescence ratio determined after addition of 10 mM Ionomycin, R$_{min}$ is the minimal ratio determined by the subsequent addition of a Ca$^{2+}$ free solution containing 5 mM EGTA, and Sf2/Sb2 is the ratio of fluorescence values at 380 nm excitation determined at R$_{min}$ and R$_{max}$, respectively.

Stimulation of THP-1 cells with hMCP-1 induced a rapid, transient rise in [Ca$^{2+}$]$_i$ in a specific and dose dependent manner. Dose response curves indicated an approximate $EC_{50}$ of 2 nm. Test compounds dissolved in DMSO (10 µl) were assayed for inhibition of calcium release by adding them to the cell suspension 10 sec prior to ligand addition and measuring the reduction in the transient rise in $[Ca^{2+}]i$. Test compounds were also checked for lack of agonist activity by addition in place of hMCP-1.

c) hMCP-1 and RANTES Mediated Chemotaxis.

In vitro chemotaxis assays were performed using the human monocytic cell line THP-1. Cell migration through polycarbonate membranes was measured by enumerating those passing through either directly by Coulter counting or indirectly by use of a colourimetric viability assay measuring the cleavage of a tetrazolium salt by the mitochondrial respiratory chain (Scudiero D. A. et al. 1988, *Cancer Res.*, 48, 4827–4833).

Chemoattractants were introduced into a 96-well microtitre plate which forms the lower well of a chemotaxis chamber fitted with a PVP-free 5 µm poresize polycarbonate adhesive framed filter membrane (NeuroProbe MB series, Cabin John, Md. 20818, USA) according to the manufacturer's instructions. The chemoattractant was diluted as appropriate in synthetic cell culture medium, RPMI 1640 (Gibco) or supplemented with 2 mM glutamine and 0.5% BSA, or alternatively with HBSS with $Ca^{2+}$ and $Mg^{2+}$ without Phenol Red (Gibco) plus 0.1% BSA. Each dilution was degassed under vacuum for 30 min and was placed (400 µl) in the lower wells of the chamber and THP-1 cells ($5 \times 10^5$ in 100 µl RPMI 1640+0.5% BSA) were incubated in each well of the upper chamber. For the inhibition of chemotaxis the chemoattractant was kept at a constant submaximal concentration determined previously (1 nM MCP-1) and added to the lower well together with the test compounds dissolved in DMSO (final DMSO concentration <0.05% v/v) at varying concentrations. The chamber was incubated for 2 h at 37° C. under 5% $CO_2$. The medium was removed from the upper wells which were then washed out with 200 µl physiological saline before opening the chamber, wiping dry the membrane surface and centrifuging the 96-well plate at 600 g for 5 min to harvest the cells. Supernatant (150 µl) was aspirated and 10 µl of cell proliferation reagent, WST-1, {4-[3-(4-iodophenyl)-2-(4-nitrophenyl)-2H-5-tetrazolio]-1, 3-phenyl disulfonate} plus an electron coupling reagent (Boehringer Mannheim. Cat.no. 1644 807) was added back to the wells. The plate was incubated at 37° C. for 3 h and the absorbance of the soluble formazan product was read on a microtitre plate reader at 450 nm. The data was input into a spreadsheet, corrected for any random migration in the absence of chemoattractant and the average absorbance values, standard error of the mean, and significance tests were calculated. hMCP-1 induced concentration dependent cell migration with a characteristic biphasic response, maximal 0.5–1.0 nm.

In an alternative form of the above assay, fluorescently tagged cells can be used in order to assist in end point detection. In this case, the THP-1 cells used are fluorescently tagged by incubation in the presence of 5 mM Calcein AM (Glycine, N,N'-[[3', 6'-bis(acetyloxy)-3-oxospiro [isobenzofuran-1(3H), 9'-[9H]xanthene]-2',7'-diyl]bis (methylene)]bis[N-[2-[(acetyloxy)methoxy]-2-oxoethyl]]-bis[(acetyloxy)methyl]ester; Molecular Probes) for 45 minutes in the dark. Cells are harvested by centrifugation and resuspended in HBSS (without Phenol Red) with $Ca^{2+}$, $Mg^{2+}$ and 0.1% BSA. 50 µl ($2 \times 105$ cells) of the cell suspension are placed on the filter above each well and, as above, the unit is incubated at 37° C. for 2 hours under 5% $CO_2$. At the end of the incubation, cells are washed off the upper face of the filter with phosphate buffered saline, the filter removed from the plate and the number of cells attracted to either the underside of the filter or the lower well estimated by reading fluorescence at 485 nm excitation, 538 nm emission wavelengths (fmax, Molecular Devices). The data was input into a spreadsheet, corrected for any random migration in the absence of chemoattractant and the average fluorescence values, standard error of the mean, percentage inhibition and $IC_{50}$ of compounds under test and significance tests can be calculated. In addition to MCP-1 induced chemotaxis, this alternative form of the assay was also used to measure inhibition of RANTES (2 nM) induced chemotaxis.

d) Binding to Human Peripheral Blood Mononuclear Cells(PBMCs)

i) Preparation of Human PBMCs

Fresh human blood (200 ml) was obtained from volunteer donors, collected into sodium citrate anticoagulant to give a final concentration of 0.38%. The blood was mixed with Sedimentation Buffer and incubated at 37° C. for 20 minutes. The supernatant was collected and centrifuged at 1700 rpm for 5 minutes (Sorvall RT6000D). The pellet obtained was resuspended in 20 ml RPMI/BSA (1 mg/ml) and 4×5mls of cells were carefully layered over 4×5 mls of Lymphoprep ä (Nycomed) in 15 ml centrifuge tubes. Tubes were spun at 1700 rpm for 30 minutes (Sorvall RT6000D) and the resultant layer of cells was removed and transferred to 50 ml Falcon tubes. The cells were washed twice in Lysis Buffer to remove any remaining red blood cells followed by 2 washes in RPMI/BSA. Cells were resuspended in 5 mls of Binding Buffer. Cell number was measured on a Coulter counter and additional binding buffer was added to give a final concentration of $1.25 \times 10^7$ PBMCs /ml.

ii) Assay

[$^{125}$I]MCP-1 was prepared using Bolton and Hunter conjugation (Bolton et al., 1973, *Biochem. J.*, 133, 529; Amersham International plc]. Equilibrium binding assays were carried out using the method of Ernst e al., 1994, *J. Immunol.*, 152, 3541. Briefly, 50 µl of $^{125}$I-labeled MCP-1 (final concentration 100 pM) was added to 40 µl ($5 \times 10^5$ cells) of cell suspension in a 96 well plate. Compounds, diluted in Whole Cell Binding Buffer from a stock solution of 10 mM in DMSO were added in a final volume of 5 µl to maintain a constant DMSO concentration in the assay of 5%. Total binding was determined in the absence of compound. Non-specific binding was defined by the addition of 5 µl cold MCP-1 to give a final assay concentration of 100 nM. Assay wells were made up to a final volume of 100 µl with Whole Cell Binding Buffer and the plates sealed. Following incubation at 37° C. for 60 minutes the binding reaction mixtures were filtered and washed for 10 seconds using ice cold Wash Buffer using a plate washer (Brandel MLR-96T Cell Harvester). Filter mats (Brandel GF/B) were pre-soaked for 60 minutes in 0.3% polyethylenimine plus 0.2% BSA prior to use. Following filtration individual filters were separated into 3.5 ml tubes (Sarstedt No. 55.484) and bound $^{125}$I-labeled MCP-1 was determined (LKB 1277 Gammamaster).

Test compound potency was determined by assay in duplicate using six point dose-response curves and $IC_{50}$ concentrations were determined.

For example. using this method, compound No. 9 in Table 1 showed an $IC_{50}$ of 12.75 µM in the hMCP-1 chemotaxis assay and compound No. 15 in Table 1 showed an $IC_{50}$ of 3.64 µM in the RANTES chemotaxis assay.

No physiologically unacceptable toxicity was observed at the effective dose for compounds tested of the present invention.

EXAMPLE 15

Pharmaceutical Compositions

The following Example illustrates, but is not intended to limit, pharmaceutical dosage forms of the invention as defined herein (the active ingredient being termed "Compound X"), for therapeutic or prophylactic use in humans:

|  | mg/tablet |
|---|---|
| (a) Tablet I | |
| Compound X. | 100 |
| Lactose Ph.Eur | 182.75 |
| Croscarmellose sodium | 12.0 |
| Maize starch paste (5% w/v paste) | 2.25 |
| Magnesium stearate | 3.0 |
| (b) Tablet II | |
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |
| (c) Tablet III | |
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

|  | mg/capsule |
|---|---|
| (d) Capsule | |
| Compound X | 10 |
| Lactose Ph.Eur | 488.5 |
| Magnesium | 1.5 |
| (e) Injection I | (50 mg/ml) |
| Compound X | 5.0% w/v |
| 1 M Sodium hydroxide solution | 15.0% v/v |
| 0.1 M Hydrochloric acid | to adjust pH to 7.6 |
| Polyethylene glycol 400 | 4.5% w/v |
| Water for injection | to 100% |
| (f) Injection II | (10 mg/ml) |
| Compound X | 1.0% w/v |
| Sodium phosphate BP | 3.6% w/v |
| 0.1 M Sodium hydroxide solution | 15.0% v/v |
| Water for injection | to 100% |
| (g) Injection III | (1 mg/ml. buffered to pH6) |
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

|  | mg/ml |
|---|---|
| (h) Aerosol I | |
| Compound X | 10.0 |
| Sorbitan trioleate | 13.5 |
| Trichlorofluoromethane | 910.0 |
| Dichlorodifluoromethane | 490.0 |
| (i) Aerosol II | |
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |
| (j) Aerosol III | |
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |
| (k) Aerosol IV | |
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

| (l) Ointment | ml |
|---|---|
| Compound X | 40 mg |
| Ethanol | 300 µl |
| Water | 300 µl |
| 1-Dodecylazacycloheptan-2-one | 50 µl |
| Propylene glycol | to 1 ml |

Note:
Compound X in the above formulation may comprise a compound illustrated in Examples herein. The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin be replaced by an alternative suspending agent such as sorbitan monooleate, sorbitan sesquioleate, polysorbate 80, polyglycerol oleate or oleic acid.

What is claimed is:

1. A compound of formula (I)

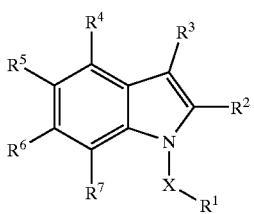

or a pharmaceutically acceptable salt, in vivo hydrolysable ester, or an N—$C_{1-6}$alkyl or N,N-di-($C_{1-6}$alkyl)amide thereof, where X is $CH_2$ or $SO_2$;

$R^1$ is in aryl optionally substituted by alkyl, alkenyl, alkynyl, halo, haloalkyl including perhaloalkyl, mercapto, alkoxy, haloalkoxy, alkenyloxy, alkynyloxy, hydroxyalkoxy, alkoxyalkoxy, alkanoyl, alkanoyloxy, cyano, nitro, amino, mono- or di-alkyl amino, oximino, sulphonamido, carbamoyl, mono or dialkylcarbamoyl or $S(O)_m R^{21}$ where m is defined above and $R^{21}$ is hydrocarbyl, $R^2$ is carboxy, cyano, —C(O)$CH_2$OH, —CONH$R^8$, —$SO_2$NH$R^9$, tetrazol-5-yl, $SO_3$H, or a group of formula (VI)

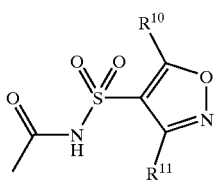

(VI)

where $R^8$ is selected from hydrogen, alkyl, aryl, cyano, hydroxy, —$SO_2R^{12}$ where $R^{12}$ is alkyl, aryl, or haloalkyl, or $R^8$ is a group-$(CHR^{13})_r$—COOH where r is an integer of 1–3 and each $R^{13}$ group is independently selected from hydrogen or alkyl; $R^9$ is hydrogen, alkyl, aryl, or a group $COR^{14}$ where $R^{14}$ is alkyl, aryl, or haloalkyl; $R^{10}$ and $R^{11}$ are independently selected from hydrogen or alkyl:

$R^3$ is hydrogen; a functional group as defined below; alkyl optionally substituted by halo, hydroxyl, or alkoxy; alkenyl; alkynyl; aryl optionally substituted by one or more groups selected from chlorine, fluorine, methyl, trifluoromethyl, trifluoromethoxy, amino, formyl, phenyl, methoxy, phenoxy or phenyl; aralkyl, aralkyloxy, or cycloalkyl;

$R^4$ is a group $OR^{15}$ or $S(O)_qR^{15}$, where q is 0, 1 or 2 and $R^{15}$ is a hydrogen-containing alkyl group substituted by at least one functional group as defined below, or an aryl group which is optionally substituted by one or more functional groups as defined below; and $R^5$, $R^6$, and $R^7$ are independently selected from hydrogen, a functional group as defined below, a hydrocarbyl group, carboxyalkyl or the amide derivative thereof;

and wherein any functional group is selected from halo, cyano, nitro, $C(O)_nR^{18}$, $OR^{18}$, $S(O)_mR^{18}$, $NR^{19}R^{20}$, $C(O)NR^{19}R^{20}$, $OC(O)NR^{19}R^{20}$, —$NR^{19}C(O)_nR^{18}$, —$NR^{18}CONR^{19}R^{20}$, —$N=CR^{18}R^{19}$, $S(O)_nNR^{19}R^{20}$, and —$NR^{19}S(O)_mR^{18}$ where $R^{18}$, $R^{19}$, and $R^{20}$ are independently selected from hydrogen or hydrocarbyl, optionally substituted by halo, perhaloalkyl, mercapto, hydroxy, carboxy, alkoxy, alkenyloxy, alkynyloxy, alkoxyalkoxy, aryloxy (where the aryl group may be substituted by halo, nitro, or hydroxy), cyano, nitro, amino, mono- or di-alkyl amino, oximino, or $S(O))_mR^{16}$ wherein m' is 1 or 2 and $R^{16}$ is alkyl, and n is an integer of 1 or 2, and m is an integer of 1–3.

2. A compound according to claim 1 wherein $R^{15}$ is a $C_{1-3}$alkyl group substituted with one or more of a functional group or aryl optionally substituted by a functional group as defined in claim 1.

3. A compound according to claim 1 or claim 2 wherein $R^{15}$ is a $C_{1-3}$alkyl group substituted with one or more groups selected from halo; hydroxy; cyano; amino, mono- or di-alkylamino wherein each alkyl group is optionally substituted by hydroxyl or alkoxy: $C_{1-4}$alkoxy; carboxy; sulphonamido; $CONH_2$; phenyl optionally substituted by carboxy, halo, hydroxy, alkoxy, carbamoyl, acyl, or hydroxyalkyl where the alkyl group suitably includes at least two carbon atoms.

4. A compound according to claim 1 or 2, where $R^4$ is a group $OR^{15}$ where $R^{15}$ is a straight or branched chain alkyl group which carries at least one hydroxy group.

5. A compound according to claim 1 or 2, wherein $R^{15}$ is a group of formula —$(CH_2)_a[(CHOH)(CH_2)_b]_dCH_2OH$ where a is an integer of from 1 to 4, b is 0 or an integer of from 1 to 4, and d is 0 or 1.

6. A compound according to claim 1 or 2, wherein $R^1$ is 3,4-dichlorophenyl, 3-fluoro-4-chlorophenyl, 3-chloro-4-fluorophenyl or 2,3-dichloropyrid-5-yl.

7. A compound according to claim 1 or 2, wherein X is $CH_2$.

8. A pharmaceutical composition comprising a compound according to claim 1 or 2, in combination with a pharmaceutically acceptable carrier.

9. A method of making a compound of formula (I) as defined in claim 1 which method comprises reacting a compound of formula (VII)

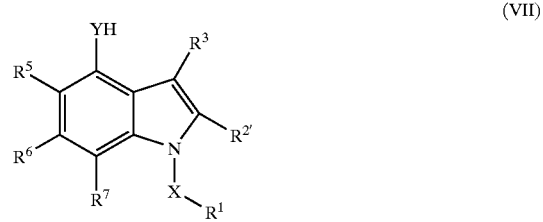

(VII)

where $R^1$, $R^3$ $R^5$, $R^6$, $R^7$ and X are as defined in relation to formula (I), $R^2$ is a group $R^2$ as defined in relation to formula (I) or a protected form thereof and Y is oxygen or sulphur with a compound of formula (VIII)

Z—$R^{15'}$ (VIII)

where Z is a leaving group and $R^{15'}$ is a group $R^{15}$ as defined in claim 1 or a precursor thereof, and thereafter if desired or necessary carrying out one or more of the following steps:

(i) converting a precursor group $R^{15'}$ to a group $R^{15}$;

(ii) converting a group $R^{15}$ to another such group;

(iii) oxidising a thiol group $R^4$ to a sulphinyl or sulphonyl group; or (iv) deprotecting a group $R^{2'}$ or converting the existing group $R^2$ to a different $R^2$ group.

* * * * *

UNITED STATES PATENT AND TRADEMARK OFFICE
CERTIFICATE OF CORRECTION

PATENT NO.    : 6,569,888 B1
DATED         : May 27, 2003
INVENTOR(S)   : Kettle et al.

It is certified that error appears in the above-identified patent and that said Letters Patent is hereby corrected as shown below:

Column 3,
Line 9, replace "bernzoxazolyl" with -- benzoxazolyl --.

Column 4,
Line 38, replace "trifluormethyl" with -- trifluoromethyl --.

Column 6,
Line 2, replace "X is $C_2$" with -- X is $CH_2$ --.
Line 63, replace "production" with -- production of the --.

Column 12,
Line 24, replace "tetralydrofuran" with -- tetrahydrofuran --.

Column 14,
Line 48, replace "croup" with -- group --.

Column 18,
Line 28, replace "el. al." with -- Et al. --.
Line 43, replace "carboxlate" with -- carboxylate --.

Column 19,
Line 32, replace "S-[N-(3,4-dichlorobenzy-2-ethoxycarbonylindol-4-yl]" with
-- S-[N-(3,4-dichlorobenzyl-2-ethoxycarbonylindol-4-yl] --.

Column 21,
Line 28, replace "halt" with -- half --.

Column 22,
Line 3, replace "describe" with -- described --.

Column 25,
Lines 29 and 30, replace "3.86 (s, 3H))," with -- 3.86 (s, 3H), --.

Column 27,
Line 25, replace "morpholinodropoxy)indole-2-carboxylic Acid" with
-- morpholinopropoxy)indole-2-carboxylic Acid --

Column 28,
Line 1, replace "N-(3,4-diclilorobenzyl)-4-" with -- N-(3,4-dichlorobenzyl)-4- --.

UNITED STATES PATENT AND TRADEMARK OFFICE
CERTIFICATE OF CORRECTION

PATENT NO. : 6,569,888 B1
DATED : May 27, 2003
INVENTOR(S) : Kettle et al.

It is certified that error appears in the above-identified patent and that said Letters Patent is hereby corrected as shown below:

Column 29,
Line 66, replace "M/z (-) 424" with -- M/z (+) 424 --.
Line 67, replace "(M-H$^+$)" with -- (MH$^+$) --.

Column 30,
Line 5, replace "3.72" with -- 3.79 --.

Column 31,
Line 8, replace "aminoberzofuran" with -- aminobenzofuran --.
Line 39, replace "(Wigler el" with -- Wigler et) --.
Line 54, replace "(Siciliano el" with -- (Siciliano et --.

Column 34,
Line 38, replace "Ernst e" with -- Ernst et --.

Column 36,
Line 28, replace "and soya lecithin" with -- and soya lecithin may --.
Line 55, replace "R$^1$ is in aryl" with -- R$^1$ is an aryl --.

Column 37,
Line 43, replace "S(O))" with -- S(O) --.
Line 44, replace "$_m$R$^{16}$" with -- $_m$'R$^{16}$ --.

Signed and Sealed this

Twenty-third Day of September, 2003

JAMES E. ROGAN
*Director of the United States Patent and Trademark Office*